United States Patent
Weiss et al.

(10) Patent No.: US 11,834,659 B2
(45) Date of Patent: Dec. 5, 2023

(54) TRANS-ACTIVATED FUNCTIONAL RNA BY STRAND DISPLACEMENT AND USES THEREOF

(71) Applicant: Massachusetts Institute of Technology, Cambridge, MA (US)

(72) Inventors: Ron Weiss, Newton, MA (US); Giulio Alighieri, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 138 days.

(21) Appl. No.: 17/032,233

(22) Filed: Sep. 25, 2020

(65) Prior Publication Data

US 2021/0095286 A1 Apr. 1, 2021
US 2021/0395732 A9 Dec. 23, 2021

Related U.S. Application Data

(60) Provisional application No. 62/906,248, filed on Sep. 26, 2019.

(51) Int. Cl.
| | | |
|---|---|---|
| *C12N 15/11* | (2006.01) | |
| *C12N 15/113* | (2010.01) | |
| *A61K 31/7105* | (2006.01) | |
| *C12N 9/22* | (2006.01) | |

(52) U.S. Cl.
CPC ........ *C12N 15/113* (2013.01); *A61K 31/7105* (2013.01); *C12N 9/22* (2013.01); *C12N 2310/122* (2013.01); *C12N 2310/141* (2013.01); *C12N 2310/20* (2017.05)

(58) Field of Classification Search
CPC .. C12N 15/113; C12N 9/22; C12N 2310/122; C12N 2310/141
See application file for complete search history.

(56) References Cited

U.S. PATENT DOCUMENTS

| | | | | |
|---|---|---|---|---|
| 2009/0098561 A1* | 4/2009 | Smolke | ................ | C12N 15/115 435/6.12 |
| 2010/0311815 A1* | 12/2010 | Chinnaiyan | ............. | A61P 35/00 435/325 |
| 2015/0004615 A1 | 1/2015 | Pierce et al. | | |

FOREIGN PATENT DOCUMENTS

| | | |
|---|---|---|
| WO | WO 2013/142735 A1 | 9/2013 |
| WO | WO 2017/223449 A1 | 12/2017 |
| WO | WO 2018/026762 A1 | 2/2018 |
| WO | WO 2018/209320 A1 | 11/2018 |

OTHER PUBLICATIONS

Hanewich-Hollatz et al., Conditional Guide RNAs: Programmable Conditional Regulation of CRISPR/Cas Function in Bacterial and Mammalian Cells via Dynamic RNA Nanotechnology. ACS Cent Sci. Jul. 24, 2019;5(7):1241-1249. doi: 10.1021/acscentsci. 9b00340. Epub Jun. 4, 2019. PMID: 31403072; PMCID: PMC6661866.
Oesinghaus et al., Switching the activity of Cas12a using guide RNA strand displacement circuits. Nat Commun. May 7, 2019;10(1):2092. doi: 10.1038/s41467-019-09953-w. PMID: 31064995; PMCID: PMC6504869.
Briner et al., Guide RNA functional modules direct Cas9 activity and orthogonality. Mol Cell. Oct. 23, 2014;56(2):333-339. doi: 10.1016/j.molcel.2014.09.019. Epub Oct. 16, 2014. PMID: 25373540.
Šulc et al., Modelling toehold-mediated RNA strand displacement. Biophys J. Mar. 10, 2015;108(5):1238-47. doi: 10.1016/j.bpj.2015. 01.023. PMID: 25762335; PMCID: PMC4375624.
PCT/US2020/052630, Dec. 10, 2020, International Search Report and Written Opinion.

* cited by examiner

*Primary Examiner* — Ekaterina Poliakova-Georgantas
(74) *Attorney, Agent, or Firm* — Wolf, Greenfield & Sacks, P.C.

(57) ABSTRACT

The present disclosure, at least in part, relates to an engineered RNA (e.g., microRNA and sgRNA), in the absence of an input signal, that is engineered to have a large enough energy gap between the formations of a first secondary structure, which is unrecognizable by an actuator, and a second secondary structure, which is recognizable by an actuator (e.g., Drosha and Cas protein).

12 Claims, 19 Drawing Sheets

Gate (B1, stable without input)

Downstream Signal (B2, more stable than B3)

Downstream Signal (B3, less stable than B2)

TRANS-ACTIVATED FUNCTIONAL RNA BY STRAND DISPLACEMENT AND USES THEREOF

RELATED APPLICATION

This application claims the benefit under 35 U.S.C. § 119(e) of U.S. provisional application No. 62/906,248 filed Sep. 26, 2019, which is incorporated by reference herein in its entirety.

FEDERALLY SPONSORED RESEARCH

This invention was made with Government support under Grant No. R01 CA207029 awarded by the National Institutes of Health. The Government has certain rights in the invention.

BACKGROUND

The current engineered RNA based technologies designed to respond to an input signal may be activated in the absence of the input signal. This side effect poses an issue to RNA based gene therapy where the activation of the engineered RNA needs to be tightly controlled.

SUMMARY

The present disclosure, at least in part, relates to an engineered RNA (e.g., microRNA and sgRNA), in the absence of an input signal, that is engineered to have a large enough energy gap between the formations of a first secondary structure at its lowest energy state, which is unrecognizable by an actuator, and a second secondary structure, which is recognizable by an actuator (e.g., Drosha and Cas protein). Such design provides the benefit of decreasing unwanted activation of the engineered RNA when the input signal is absent. When the input signal is present, it induces a conformational change of the engineered RNA molecule, such that the engineered RNA forms the second secondary structure not at its lowest energy state, which is recognizable by an actuator.

The present disclosure relates to engineered RNAs that are designed so that they can interact with an actuator only in the presence of an input signal, and are thus more specific in exerting their activity. An engineered RNA that is similar to those described in the present disclosure but is less specific, and more likely to refold into a conformation that could interact with an actuator even in the absence of an input signal, could exert many deleterious effects if its activity targets a critical host gene or mRNA. The consequences of these off-target effects are a major limitation in the development of new gene therapies, and so current therapies are restricted to targeting certain mRNAs, such as viral RNAs in virally infected cells, to minimize off-target effects and maximize safety.

The engineered RNAs described in the present disclosure are specific, being unlikely to exert any activity in the absence of input signal. A major benefit of this increased specificity is that if they reliably exert activity only in cells containing the input signal, that activity can be directed towards the most effective target, even if that target is a gene that is essential for cellular replication. In the treatment of virally infected cells, for example, engineered RNAs such as the ones described in the present disclosure are not limited to targeting viral mRNAs, but may also target genes or mRNAs encoding host factors that are essential for viral replication. This increased specificity allows the engineered RNAs described in the present disclosure to target more genes or mRNAs, improving their therapeutic efficacy without compromising safety.

In some aspects, the present disclosure provides an engineered RNA comprising: (i) an effector portion; and (ii) a responder sequence, wherein the effector portion comprises a coding sequence for a functional RNA, wherein, in the absence of a input signal, the engineered RNA forms a first secondary structure in which the engineered RNA is not capable of being recognized by an actuator; and wherein, in the presence of the input signal, the responder sequence is capable of responding to the input signal such that the engineered RNA forms a second secondary structure, not at its lowest energy state, in which the engineered RNA is capable of being recognized by the actuator.

In some embodiments, the effector portion comprises the coding sequence for a pre-microRNA (pre-miRNA).

In some embodiments, the engineered RNA comprises parts T-d-f-e-b-S-a-c, wherein the coding sequence for a pre-miRNA comprises parts b-S-a; wherein the responder sequence comprises parts T-d-f-e; wherein the actuator is Drosha; wherein, in the absence of an input signal which comprises an input RNA that is completely or partially complementary to parts T-d-f, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha; wherein, in the presence of the input RNA that is completely or partially complementary to parts T-d-f, the engineered RNA forms a secondary structure in which parts T-d-f form a double strand with the input RNA, thereby releasing part e from part f and part b from part d, and in which part a partially hybridizes to part b to form a Drosha recognizable cleavage site not at its lowest energy state.

In some embodiments, the engineered RNA comprises, parts T-f-d-c-a-S-b-e, wherein the coding sequence for a pre-miRNA comprises parts b-S-a; wherein the responder sequence comprises parts T-f-d and e; wherein the actuator is Drosha; wherein, in the absence of an input signal which comprises an input RNA that is completely or partially complementary to parts T-f-d, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha; wherein, in the presence of the input RNA that is completely or partially complementary to parts T-f-d, the engineered RNA forms a secondary structure in which parts T-f-d form a double strand with the input RNA, thereby releasing part e from part f and part b from part d, and in which part a partially hybridizes to part b to form a Drosha recognizable cleavage site not at its lowest energy state.

In some embodiments, the engineered RNA comprises parts 5' hairpin-toehold-antisense-ribozyme-stem-seed-sense-3' hairpin, wherein the coding sequence for a pre-miRNA comprises parts stem-seed-sense; wherein the responder sequence comprises parts toehold-antisense-ribozyme; wherein the actuator is Drosha; wherein, in the absence of an input signal which comprises an input RNA that is completely or partially complementary to parts toehold-antisense-ribozyme, the engineered RNA forms a first secondary structure in which part 5' hairpin completely or partially hybridizes to itself, part antisense completely or partially hybridizes to part sense, part ribozyme completely or partially hybridizes to itself, part stem completely or partially hybridizes to itself, part seed completely or partially hybridizes to itself, part 3' hairpin completely or partially hybridizes to itself, and part stem is incapable of hybridizing to part sense, such that the engineered RNA is not capable of being recognized by Drosha; wherein, in the presence of the input RNA that is completely or partially complementary to parts toehold-sense-ribozyme, the engineered RNA forms a secondary structure in which parts toehold-antisense-ribozyme hybridize with the input RNA, resulting in ribozyme-mediated cleavage that releases an RNA waste product comprising the input RNA hybridized to parts 5' hairpin-toehold-sense and a portion of part ribozyme of the engineered RNA, wherein, following the release of the RNA waste product, the remaining portion of the engineered RNA forms a secondary structure in which part stem partially or completely hybridizes to part sense to form a Drosha recognizable cleavage site not at its lowest energy state.

In some embodiments, miRNA is therapeutic miRNAs selected from the group consisting of miR-16, miR-29, miR-34, miR-143, miR-145, and miR-200 family.

In some embodiments, the effector portion comprises the coding sequence for a single guide RNA (sgRNA).

In some embodiments, the engineered RNA is an engineered sgRNA comprising: parts S-g-a-c-T-d-f-e-b-h; wherein the coding sequence for sgRNA comprises part S-g-a and b-h, wherein the responder sequence comprises parts c-T-d-f-e, wherein the actuator is a Cas protein, wherein, in the absence of an input signal which comprises an input RNA that is completely or partially complementary to parts T-d-f, the engineered RNA forms a first secondary structure in which part d partially hybridizes to part b, part e completely or partially hybridizes to part f, part a completely or partially hybridizes to part c, part g hybridizes to part h, and parts a and b are incapable of hybridizing with each other; wherein, in the presence of the input RNA that is completely or partially complementary to parts T-d-f, the engineered RNA forms a second secondary structure in which parts T-d-f form a double strand with the input RNA, thereby releasing part e from part f and part b from part d, and in which part a partially hybridizes to part b to form a Cas protein binding site not in its lowest energy state.

In some embodiments, the engineered RNA is an engineered sgRNA comprising, comprising: parts S-g-b-e-f-d-T-c-a-h; wherein the coding sequence for sgRNA comprises part S-g-b and a-h; wherein the responder sequence comprises parts e-f-d-T-c, wherein the actuator is a Cas protein, wherein, in the absence of an input signal which comprises an input RNA that is completely or partially complementary to parts T-d-f, the engineered RNA forms a first secondary structure in which part d completely or partially hybridizes to part b, part e completely or partially hybridizes to part f, part a completely or partially hybridizes to part c, part g hybridizes to part h, and parts a and b are incapable of hybridizing with each other; wherein, in the presence of the input RNA that is completely or partially complementary to parts T-d-f, the engineered RNA forms a second secondary structure in which parts T-d-f form a double strand with the input RNA, thereby releasing part e from part f and part b from part d, and in which part a partially hybridizes to part b to form a Cas protein binding site not at its lowest energy state. In some embodiments, the engineered RNA further comprises a nexus and hairpins.

In some embodiments, the Cas protein selected from a group consisting of Cas9, saCas9, CjCas9, xCas9, Cas13a/C2c2, Cas13b, Cpf1 and variants thereof. In some embodiments, the Cas protein is a Cas9 fusion protein selected from a group consisting of dCas9-transcription factor, dCas9-VP64, dCas9-VPR, dCas9-Suntag, dCas9-P300, dCas9-VP160, dCas9VP192, dCas9-KRAB and its derivative, dCas9- MXI1, dCas9-SID4X, dCas9-LSD1, dCas9-CIB1, dCas9-GFP, and dCas9-RFP.

In some aspects, the present disclosure also provides an engineered nucleic acid, comprising a promoter operably linked to a nucleotide sequence encoding the engineered RNA described herein.

In some aspects, the present disclosure also provides a recombinant virus comprising: a viral capsid containing a promoter operably linked to a nucleotide sequence encoding the engineered RNA described herein. In some embodiments, the recombinant virus is a recombinant AAV (rAAV). In some embodiments, the recombinant virus is a recombinant lentivirus, adeno virus, or a bacteriophage.

In some aspects, the present disclosure also provides a host cell, comprising the engineered RNA, the engineered nucleic acid, or the recombinant virus, as described herein. In some embodiments, the host cell is a prokaryotic cell. In some embodiments, the prokaryotic cell is a bacterial cell. In some embodiments, the host cell is a eukaryotic cell. In some embodiments, the eukaryotic cell is a fungal cell, a plant cell, an insect cell, or a mammalian cell. In some embodiments, the mammalian cell is a human cell. In some embodiments, the host cell is a diseased cell. In some embodiments, the host cell is from a specific tissue. In some embodiments, the host cell comprises the input signal. In some embodiments, the host cell is capable of processing the engineered RNA of described herein to produce the functional RNA.

In some aspects, the present disclosure also provides a pharmaceutical composition, comprising the engineered RNA, the engineered nucleic acid, the recombinant virus, or the cell described herein. In some embodiments, the pharmaceutical composition further comprises a pharmaceutically acceptable carrier.

In some aspects, the present disclosure also provides a method comprising delivering the engineered RNA, the engineered nucleic acid, the recombinant virus, the cell, or the pharmaceutical composition described herein to a subject in need thereof.

In some aspects, the present disclosure also provides a method for delivering a functional RNA to a cell in a subject in need thereof, comprising administering to the subject an effective amount of the engineered RNA, the engineered nucleic acid, the recombinant virus of any one, the cell of, or the pharmaceutical composition described herein.

In some aspects, the present disclosure also provides A method for treating a disease in a subject in need thereof, comprising administering to the subject an effective amount of the engineered RNA, the engineered nucleic acid, the recombinant virus of any one, the cell of, or the pharmaceutical composition described herein. In some embodiments, the subject is a human or a non-human mammal. In some embodiments, the subject has or is at risk of having Sickle Cell Disease, X-linked severe combined immunodeficiency (SCID-X1), Hurler Syndrome, Gaucher Disease, Wiskot-Aldrich syndrome, human immunodeficiency virus (HIV), Hepatitis B, human papillomavirus (HPV), Herpesviruses, Cystic Fibrosis, B-thalassemia, Retinitis Pigmentosa, amyotrophic lateral sclerosis (ALS), BEST disease, Parkinson's Disease, Schizophrenia, or severe combined immunodeficiency (SCID).

In some embodiments, wherein the engineered RNA is an engineered sgRNA, further comprising delivering Cas protein prior to or concurrently with the engineered RNA. In some embodiments, wherein the Cas protein is saCas9, and wherein the saCas9 is delivered by a rAAV comprising an rAAV capsid enclosing a promoter operably linked to a saCas9 coding sequence, the promoter and the saCas9 coding sequence being flanked by AAV ITRs. In some embodiments, the Cas protein is not saCas9, and wherein the Cas protein is delivered by a first rAAV comprising an rAAV capsid enclosing a promoter operably linked to a first portion of saCas9 coding sequence, the promoter and the first portion of the saCas9 coding sequence being flanked by AAV ITRs; and a second rAAV comprising an rAAV capsid enclosing a promoter operably linked to a second portion of saCas9 coding sequence, the promoter and the second portion of the saCas9 coding sequence being flanked by AAV ITRs

BRIEF DESCRIPTION OF DRAWINGS

FIG. 1A: B1=folding state of B when A-B is at the lowest energy state; B1*=folding state of B immediately after input interact with A. B2=folding state of B at the lowest energy when the input interact with A. FIG. 1B: B1, and B2 represent different RNA folding of the same RNA strand, the one processed by the actuator. FIGS. 1C-1D show an improved design of RNA folding: engineering an energy gap to reduce unwanted side reactions. FIG. 1C: B1=folding state of B when A-B is at the lowest energy state; B2=folding state of B at the lowest energy when the input interact with A; B3=folding state of B that can interact with the actuator. FIG. 1D shows a design with B3 at an energy state higher than the lowest. B1, B2 and B3 represent different RNA folding of the same RNA strand, the one processed by the actuator. FIG. 1E shows the possibility of the engineered energy gap being too large for the actuator to interact with B3 in the presence of the input. FIG. 1F shows the possibility of the engineered energy gap being too low to impede actuator to interact with B3 in the absence of the input.

FIG. 3A shows one of the designs for trans-activated miRNA by the use of strand displacement. FIG. 3B shows identifying the maximum energy gap in transactivating miRNA. X axis=Energy gap (Kcal/mol) between the lowest energy state (the one characterizing B in the B2 folding state, which is its lowest energy state after the interaction with the input), which Drosha cannot process, and the energy state accessible by Drosha (the one characterizing B in B3 folding state). FIGS. 3C-3D show detained design of one of the trans-activated miRNA. FIG. 3E-3F shows additional designs of the trans-activating RNA. FIG. 3G shows trans-activated miRNA by the use of the strand displacement reaction: experimental validation in mammalian cells. 30 folds activation at high transfection marker. A trans activated miRNA can be delivered through AAV without the use of exogenous proteins.

FIG. 4A shows one of the designs for trans-activated sgRNA by the use of strand displacement. FIGS. 4B-4C show trans-activated gRNA for CAS9: Energy gap for the gRNA. An actual gRNA sequence is shown in the conformation B2 (FIG. 4B) and B3 (FIG. 4C). The folding is computed with mFold. FIG. 4D-4E shows two different designs of the trans-activating sgRNA. FIG. 4F shows trans-activated sgRNA by the use of the strand displacement reaction: experimental validation in mammalian cells.

FIG. 6B shows the structure of the RNA in the absence of input signal, which is the most stable conformation and corresponds to the lowest energy state B1 in FIG. 1. FIG. 6C-6D shows two possible folding states of the RNA that may result after hybridization with an input RNA sequence, the release of an RNA waste product by the ribozyme domain of the RNA, and refolding of the remaining portion of the RNA molecule. The folding state shown in FIG. 6C is more stable and corresponds to the lower energy state B2 in FIG. 1, which cannot be processed by Drosha. The folding state shown in FIG. 6D is less stable and corresponds to the higher energy state B3 in FIG. 1, which can be processed by Drosha.

DETAILED DESCRIPTION

Figure 1A:
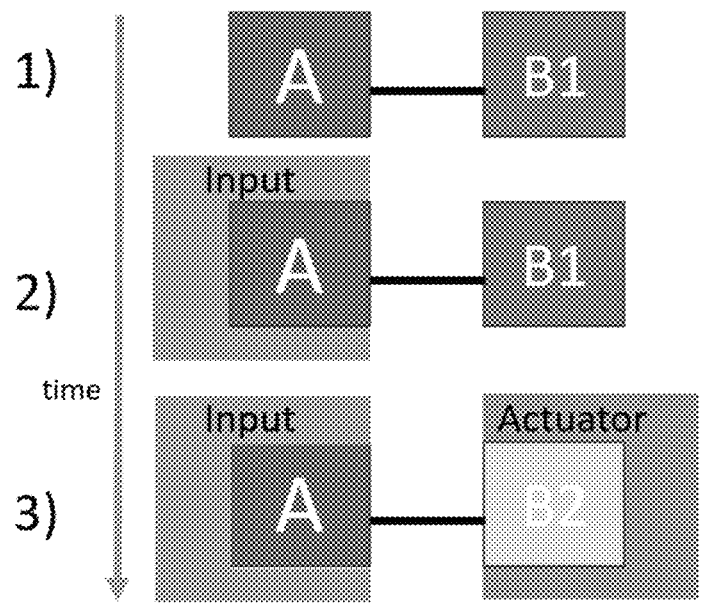
FIGS. 1A-1F show the basic concept of an RNA having a portion that interacts with the input signal, and another portion that interacts with an actuator.

The present disclosure, at least in part, relates to an engineered RNA (e.g., microRNA and sgRNA), in the absence of an input signal, that is engineered to have a large enough energy gap between the formations of a first secondary structure at its lowest energy state, which is unrecognizable by an actuator, and a second secondary structure, which is recognizable by an actuator (e.g., Drosha and Cas protein). Such design provides the benefit of decreasing unwanted activation of the engineered RNA when the input signal is absent. When the input signal is present, it induces a conformational change of the engineered RNA molecule, such that the engineered RNA forms the second secondary structure, not at its lowest energy state, which is recognizable by an actuator.

I. ENGINEERED TRANS-ACTIVATING RNA

RNA transcripts fold into secondary structures via intricate patterns of base pairing. These secondary structures impart catalytic, ligand binding, and scaffolding functions to a wide array of RNAs, forming a critical node of biological regulation. Among their many functions, RNA structural elements modulate epigenetic marks, alter mRNA stability and translation, regulate alternative splicing, transduce signals, and scaffold large macromolecular complexes. It is of crucial importance that an RNA molecule folds into a correct secondary confirmation to elicit its intended function. Of the many factors that may affect the formation of an RNA secondary structure, thermodynamics is a major determinant. Normally, an RNA favors a secondary structures that requires the lowest free energy. Such secondary structure can be defined as a secondary structure at its lowest energy state. In response to various input signals, the RNA molecule is also capable of overcoming the free energy barrier (energy gap) to form various higher energy state secondary structures that requires more free energy. Sometimes, the energy gap between the lowest energy state to the higher energy state is not great enough, and the RNA is capable of forming the higher energy state second structure in the absence of the input signal. This phenomenon poses significant issues in engineered RNA circuit in mammalian cells. The present disclosure provides an engineered RNA molecule for the purpose of increasing the energy gap between the lowest energy state structure and the higher energy state, such that the confirmation switch would only happen when the input signal is present.

Trans-activated engineered RNA, as used herein, refers to engineered RNA molecules that is triggered either by biological processes or by artificial means, through the presence of an input signal. As used herein, the term "engineered RNA" and "trans-activated engineered RNA" are used interchangeably.

In some aspects, the present disclosure provides an engineered RNA comprising (i) an effector portion; and (ii) a responder sequence. In some embodiments, the effector portion comprises a coding sequence for a functional RNA; in the absence of a input signal, the engineered RNA forms a first secondary structure in which the engineered RNA is not capable of being recognized by an actuator; and in the presence of the input signal, the responder sequence is capable of responding to the input signal such that the engineered RNA forms a second secondary structure, not at its lowest energy state, in which the engineered RNA is capable of being recognized by the actuator. Any RNA that owes its function to the secondary structure of the RNA can be engineered, and is within the scope of the present disclosure. Non-limiting examples of such RNAs are: microRNA, small interference RNA (siRNA), small hairpin RNA (shRNA), ribozymes, transfer RNA (tRNA), or single guide RNA (sgRNA). In some embodiments, the engineered RNA is an engineered pre-miRNA sequence. In some embodiments, the engineered RNA is an engineered single guide RNA.

An effector portion of the engineered RNA, as used herein, refers to the portion of the RNA that can be processed into a function RNA. In some embodiments, the effector portion comprises the coding sequence of a pre-microRNA (pre-miRNA). In some embodiments, the effector portion comprises the coding sequence of a single guide RNA (sgRNA).

A responder sequence, as used herein, refers to the sequence that is capable of interacting with the input signal, and induces the conformational change of the engineered RNA.

An input signal, as used herein, refers to a signal that is provided to the engineered RNA in order to induce its conformational change. Non-limiting examples of an input signal is a oligonucleotide sequence (e.g., DNA and RNA), a protein (e.g., RNA binding protein), or a small molecule (e.g., a small molecule that binds to RNA). In some embodiments, the input signal is an oligonucleotide sequence. In some embodiments, the input signal is an RNA. In some embodiments, the input signal is an RNA that is partially or completely complementary to the responder sequence of the engineered RNA. In some embodiments, the input signal is an endogenous signal produced by the cell. In some embodiments, the input signal is an exogenous signal supplied to the cell.

An actuator, as used herein, refers to the molecule that is capable of recognizing the secondary structure of the engineered RNA such that the RNA can elicit its downstream function. Non-limiting examples of an actuator is a oligonucleotide sequence (e.g., DNA and RNA), a protein (e.g., endoribonucleases), or a small molecule (e.g., a small molecule that binds to RNA), In some embodiments, the actuator is a protein. In some embodiments, the actuator is an endogenous protein. In some embodiments, the actuator is a protein that is involved in miRNA biogenesis. In some embodiments, the actuator is Dicer. In some embodiments, the actuator is Drosha, a Class 2 ribonuclease III enzyme that is encoded by the DROSHA gene in humans. Drosha is a nuclear dsRNA ribonuclease that processes of pri-miRNA to pre-miRNA. In other embodiments, the actuator is an exogenous protein that needs to be supplied with the input signal to the cell. In some embodiments, the actuator is a Cas protein.

Figure 2:
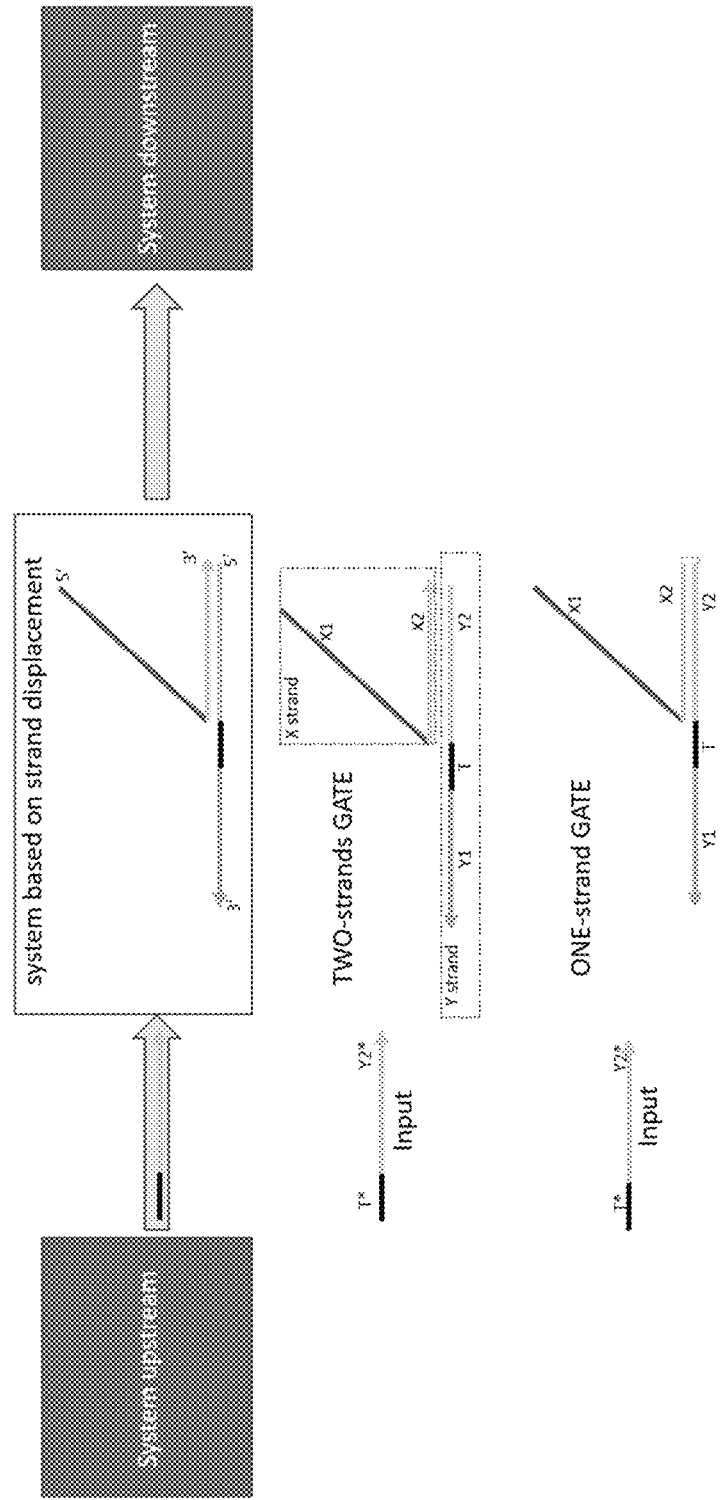
FIG. 2 shows strand displacement: input, gate and the toehold mediated reaction.

In some embodiments, the input signal interacts with the responder sequence of the engineered RNA and induces the conformational change by toehold mediated strand displacement. Strand displacement, as used herein, refers to an enzyme-free molecular tool to exchange one strand of DNA or RNA (output) with another strand (input). It is based on the hybridization of two complementary strands of DNA or RNA via Watson-Crick base pairing (A-T/U and C-G) and makes use of a process called branch migration. (Yurke et al., A DNA-fuelled molecular machine made of DNA, Nature. 406 (6796): 605-8.). Originally, the toehold-mediated strand displacement reaction has been used in cell free settings. There, an input (e.g., single strand DNA or RNA) interacts with a double stranded DNA or RNA. As shown in FIG. 2, the input domain T* (Toehold), anneal by Watson and Crick base pairing to the complementary T domain on the double stranded DNA or RNA, and then the domain Y2* displaces Y2. In some embodiments, the input can itself be the output of an upstream system, and the output of the strand displacement reaction can be the input of a system downstream. Toehold strand displacement in the use of RNA nanotechnology based on thermodynamics has been previous described. (See, e.g., Sulc et al., "Modelling Toehold-Mediated RNA Strand Displacement." Biophys J. 2015 Mar. 10; 108(5): 1238-1247.), the entire contents of which is incorporated herein by reference.

(i) Engineered RNA for miRNA Processing

In some embodiments, the engineered RNA described herein, can be designed to control the biogenesis of an miRNA in response to an input signal.

Mature microRNAs (miRNAs) are small single-stranded, non-coding RNAs (about 22 nucleotides in length), which play significant regulatory roles in various biological processes of animals, plants and viruses. There are two other forms of miRNAs: primary miRNAs (pri-miRNAs) and precursor microRNAs (pre-miRNAs). Mature miRNAs are cleaved from~90nt pre-miRNAs which are derived from the processing of a long pri-miRNA by a ribonucluease. In some embodiments, the engineered RNA comprises a pre-miRNA sequence and additional flanking sequence, including the responder sequence, at both the 5' and 3' end. In some embodiments, engineered RNA forms secondary structure that is not recognizable by Drosha at its lowest energy state in the absence of an input signal. In some embodiments, when the input signal (e.g., an RNA) is present, the engineered RNA is promoted to form a secondary structure that resembles a pri-miRNA, which is recognizable by Drosha. Such secondary structure is formed not at its lowest energy state. In some embodiments, formation of such secondary structure enables Drosha to cleave the pri-miRNA off of the engineered RNA, thereby activating the biogenesis of the encoded miRNA. In some embodiments, the input signal triggers the conformational change by hybridizing to the responder sequence, thereby displacing the responder sequence from the sequence it originally hybridized to, which allows the secondary structure recognizable by Drosha to form. In some embodiments, the input signal triggers a conformational change by hybridizing to the responder sequence, thereby activating the ribozyme domain of the responder sequence, which causes the release of an RNA waste product and allows the secondary structure recognizable by Drosha to form.

In some embodiments, the engineered RNA comprises parts T-d-f-e-b-S-a-c. In some embodiments, the coding sequence for a pre-miRNA comprises parts b-S-a; the responder sequence comprises parts T-d-f-e; and the actuator is Drosha. In some embodiments, in the absence of an input signal which comprises an input RNA that is completely or partially complementary to parts T-d-f, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha. In some embodiments, in the presence of the input RNA that is completely or partially complementary to parts T-d-f, the engineered RNA forms a secondary structure in which parts T-d-f form a double strand with the input RNA, thereby releasing part e from part f and part b from part d, and in which part a partially hybridizes to part b to form a Drosha recognizable cleavage site not at its lowest energy state. (FIG. 3E, top panel). In some embodiments, the engineered RNA, from 5' to 3', comprises T-d-f-e-b-S-a-c. In other embodiments, the engineered RNA, from 5' to 3', comprises c-a-S-b-e-f-d-T.

In other embodiments, the engineered RNA comprises parts T-f-d-c-a-S-b-e. In some embodiments, the coding sequence for a pre-miRNA comprises parts b-S-a; the responder sequence comprises parts T-f-d and e; and the actuator is Drosha. In some embodiments, in the absence of an input signal which comprises an input RNA that is completely or partially complementary to parts T-f-d, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha. In some embodiments, in the presence of the input RNA that is completely or partially complementary to parts T-f-d, the engineered RNA forms a second secondary structure in which parts T-f-d form a double strand with the input RNA, thereby releasing part e from part f and part b from part d, and in which part a partially hybridizes to part b to form a Drosha recognizable cleavage site not at its lowest energy state. (FIG. 3E, bottom panel). In some embodiments, the engineered RNA, from 5' to 3', comprises T-f-d-c-a-S-b-e. In other embodiments, the engineered RNA, from 5' to 3', comprises e-b-S-a-c-d-f-T.

As used herein, the term "hybridize" or "hybridization" means annealing of a single-stranded deoxyribonucleic acid (DNA) or ribonucleic acid (RNA) molecule to a complementary DNA or RNA or to a complementary portion of itself to form a partially double-stranded molecule. In molecular biology, "complementary" or "complementarity" describes a relationship between two structures each following the lock-and-key principle. Complementarity is achieved by distinct interactions between pairs of nucleobases: adenine and thymine (uracil in RNA); and guanine and cytosine. Adenine and guanine are purines, while thymine, cytosine and uracil are pyrimidines. Purines are larger than pyrimidines. Both types of molecules complement each other and can only base pair with the opposing type of nucleobase. In nucleic acid, nucleobases are held together by hydrogen bonding, which only works efficiently between adenine (A) and thymine (T) or uracil (U), and between guanine (G) and cytosine (C). The base pair A=T (or A=U) shares two hydrogen bonds, while the base pair G≡C has three hydrogen bonds. All other configurations between nucleobases would hinder hybridization. DNA strands are oriented in opposite directions, they are said to be antiparallel. The degree of complementarity between two nucleic acid strands may vary, from complete complementarity (each nucleotide is across from its opposite), partially complementary, to no complementarity (each nucleotide is not across from its opposite) and determines the stability of the sequences to be together. Generally speaking, the level of complementarity and the percentage of G≡C pair affect the stability of the double strand, and may require higher free energy to separate the double strand.

Any known miRNA can be engineered based on the principle described herein. Non-limiting examples of such microRNAs are: FF4, FF5, hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-127-3p, hsa-miR-1271-3p, hsa-miR-1271-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-1287-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR-142-3p, hsa-miR-142-5p, hsa-miR-143-3p, hsa-miR-143-5p, hsamiR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p,hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-197-3p, hsa-miR-197-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-5p, hsa-miR-19b-3p, hsa-miR-200a-3p, hsa-miR-200a-5p, hsa-miR-200b-3p, hsa-miR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG_miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsa-miR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsa-miR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR-484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR-495-5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsamiR-617, hsa-miR-619-5p, hsa-miR-624-3p, hsa-miR-624-5p, hsa-miR-625-3p, hsa-miR-625-5p, hsa-miR-627-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR-758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR-874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

(ii) Engineered RNA for sgRNA Biogenesis

In some embodiments, the engineered RNA described herein, can be design to control the biogenesis of a single guide (sgRNA) in response to an input signal.

sgRNA, as used herein, refers to an sgRNA is a single RNA molecule that contains both the custom-designed short crRNA sequence fused to the scaffold tracrRNA sequence. sgRNA can be synthetically generated or made in vitro or in vivo from a DNA template. It is known in the art that the sgRNA forms a secondary structure that facilitates the binding and the endonuclease activity of Cas protein. An sgRNA includes the following structural components: spacer sequence, low stem, bulge, upper stem, nexus, and hairpins. Individual functional modules of the sgRNA was described in Briner et al., 2014, Guide RNA functional modules direct Cas9 activity and orthogonality, Mol Cell. 2014 Oct. 23; 56(2):333-339. doi: 10.1016/j.molcel.2014.09.019. Epub 2014 Oct. 16. The spacer sequence dictates Cas protein localization within the genome. The lower stem is formed by the duplex between the CRISPR repeat sequence from the crRNA and the region of complementarity in the tracrRNA. Cas protein interacts with the upper and lower stems in a sequence-independent manner, whereas the bulge interactions with Cas protein appear to be sequence-dependent. The nexus contains both sequence and structural features necessary for DNA cleavage and lies at the center of the sgRNA: Cas protein interactions. The nexus also forms a junction between the sgRNA and both Cas protein and the target DNA. The terminal hairpins assist in stabilizing the sgRNA and supports stable complex formation with SpCas9. In some embodiments, the sgRNA can be engineered to form a secondary structure that is unrecognizable by Cas protein at its lowest energy state in the absence of an input signal. In some embodiments, the lower stem, the bulge, the upper stem, the nexus or the hairpins can be engineered such that the engineered sgRNA does not form the secondary structure that is recognizable by Cas protein at its lowest energy state. In some embodiments, the upper stem and the bulge are engineered to incorporate additional sequences, including the responder sequence, that would hinder the formation of the upper stem and the bulge at its lowest energy state in the absence of an input signal. In some embodiments, when the input signal (e.g., an RNA) is present, the input signal triggers a conformational change of the engineered sgRNA such that it forms the secondary structure that is recognizable by the Cas protein not at its lowest energy state. In some embodiments, the input signal triggers the conformational change by hybridizing to the responder sequence, thereby displacing the responder sequence from the sequence it originally hybridized to, which allows the secondary structure recognizable by Cas protein to form.

Figure 4A:
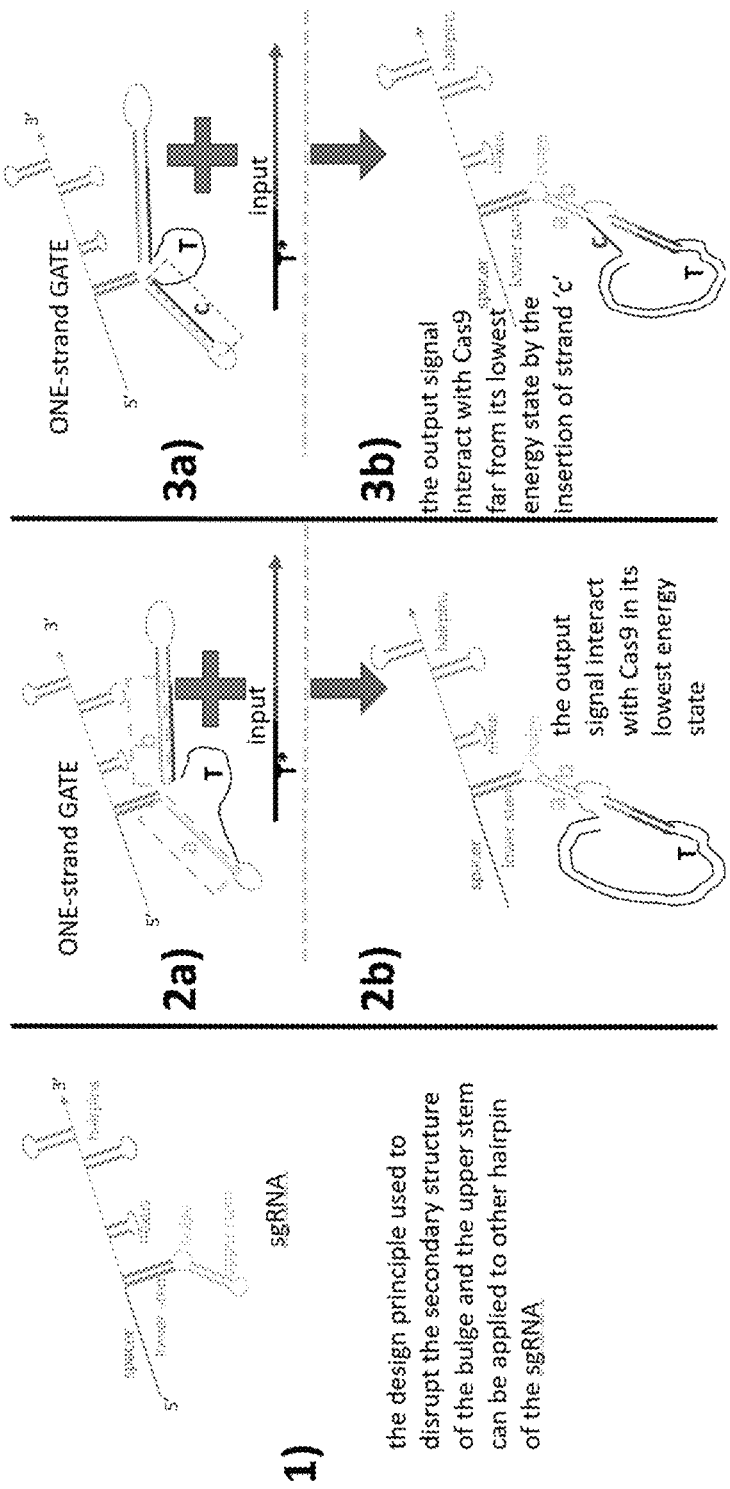
FIG. 4A-4F shows a design of engineering trans-activated sgRNA by the use of the strand displacement reaction.
Figure 4B:
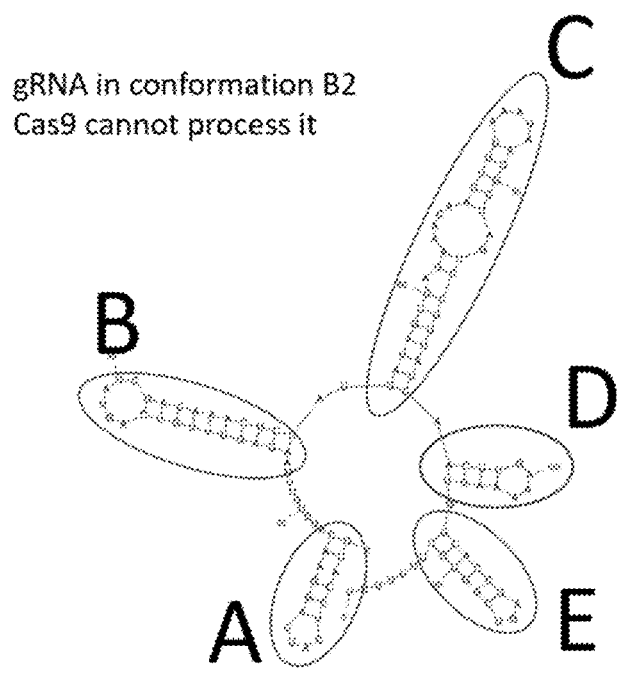
Figure 4C:
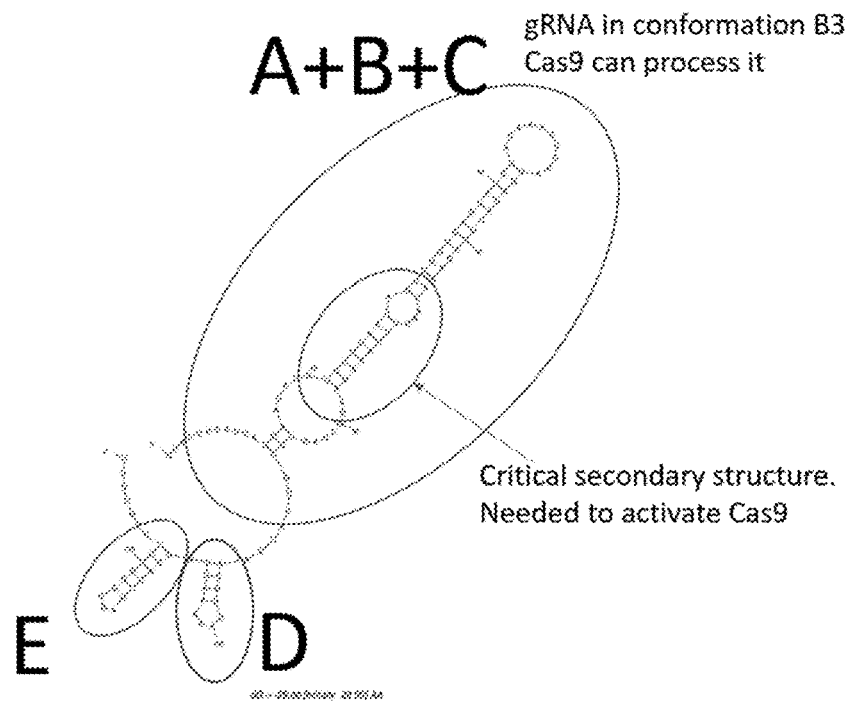
Figure 4D:
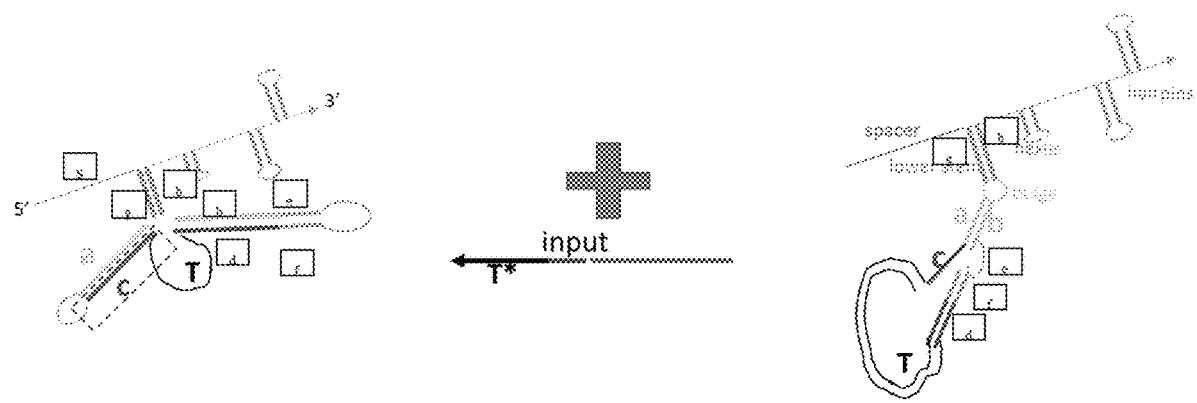

In some embodiments, the engineered RNA is an engineered sgRNA comprising: parts S-g-a-c-T-d-f-e-b-h (FIG. 4D, left panel). In some embodiments, the coding sequence for sgRNA comprises part S-g-a and b-h. In some embodiments, the responder sequence comprises parts c-T-d-f-e. In some embodiments, the actuator is a Cas protein. In some embodiments, in the absence of an input signal which comprises an input RNA that is completely or partially complementary to parts T-d-f, the engineered RNA forms a first secondary structure in which part d partially hybridizes to part b, part e completely or partially hybridizes to part f, part a completely or partially hybridizes to part c, part g hybridizes to part h, and parts a and b are incapable of hybridizing with each other. In some embodiments, in the presence of the input RNA that is completely or partially complementary to parts T-d-f, the engineered RNA forms a second secondary structure in which parts T-d-f form a double strand with the input RNA, thereby releasing part e from part f and part b from part d, and in which part a partially hybridizes to part b to form a Cas protein binding site not in its lowest energy state.

Figure 4E:
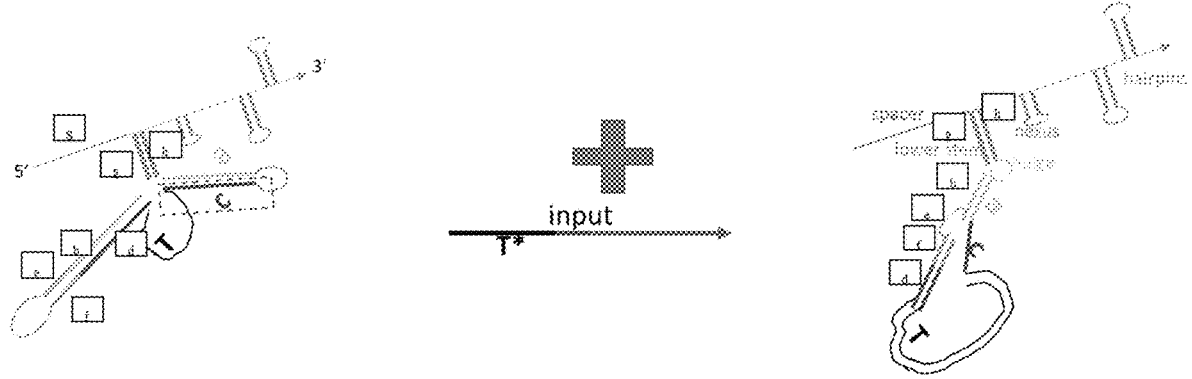
Figure 4F:
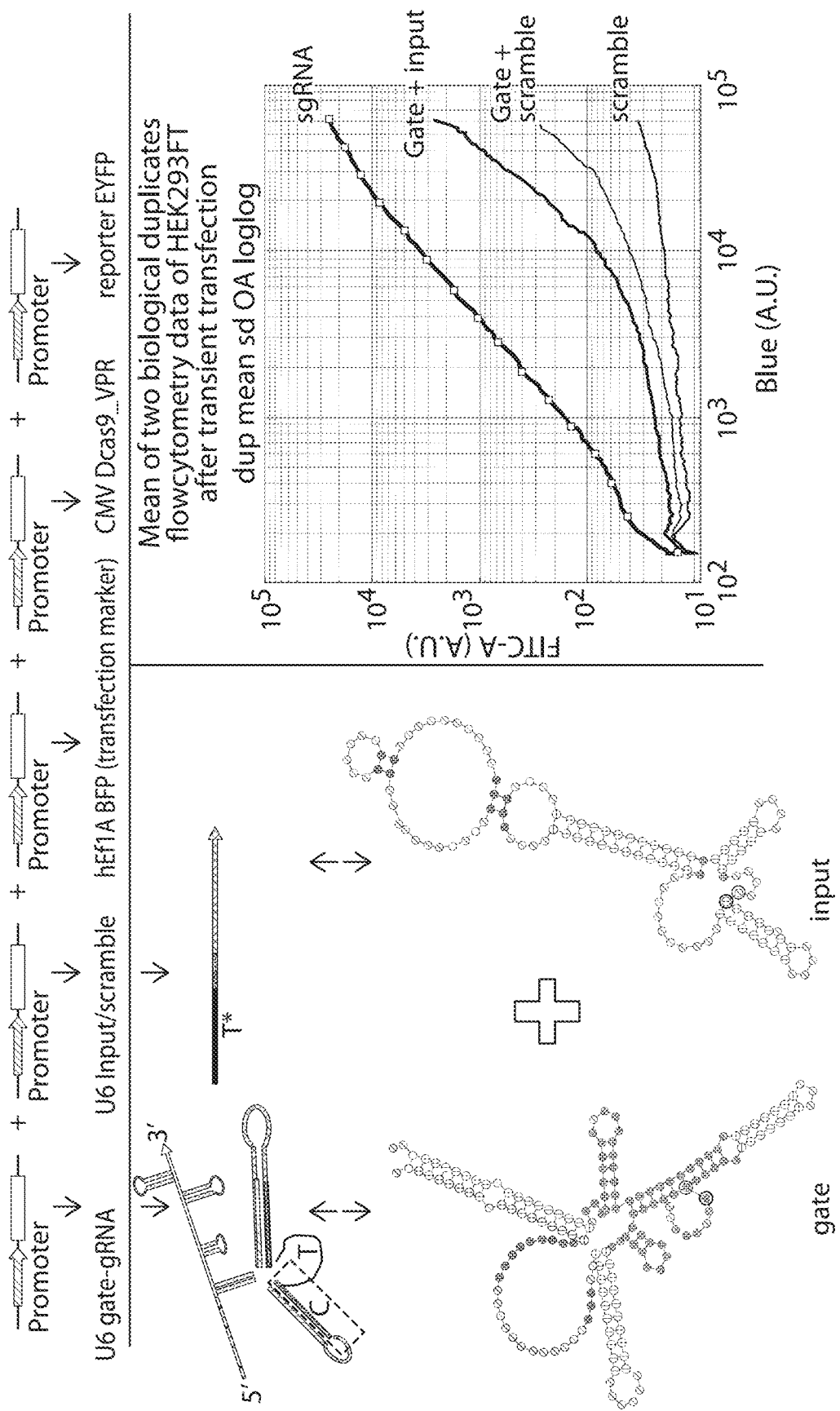
Figure 5A:
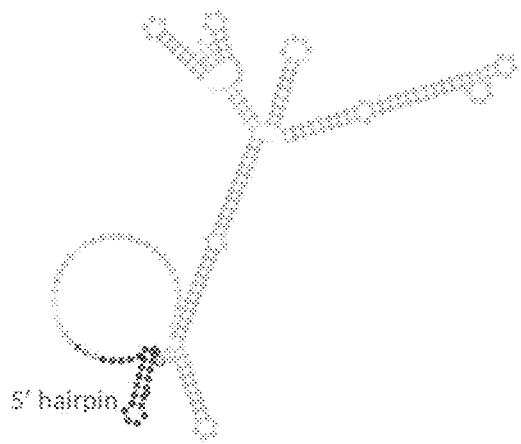
FIG. 5A-5H shows the position of different RNA domains on an exemplary trans-activated miRNA, including 5' hairpin sequence (FIG. 5A), toehold sequence (FIG. 5B), antisense sequence (FIG. 5C), ribozyme sequence (FIG. 5D), stem sequence (FIG. 5E), seed sequence (FIG. 5F), sense sequence (FIG. 5G), 3' hairpin sequence (FIG. 5H). In each, bases shown in dark color correspond to the named domain, while bases shown in lighter color correspond to the rest of the RNA. In each, the 5' guanine base is circled in blue, while the 3' uracil base is circled in red.
Figure 5B:
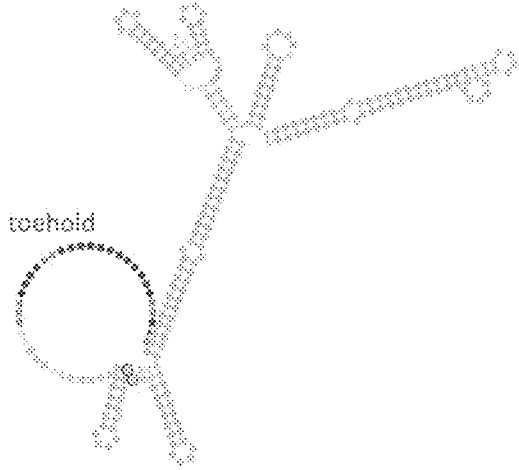
Figure 5C:
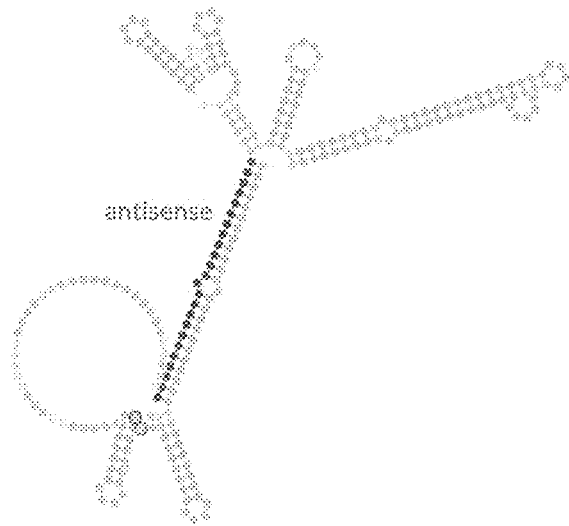
Figure 5D:
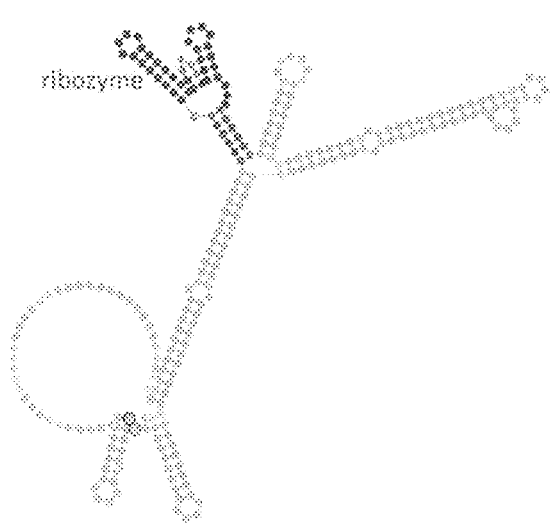
Figure 5E:
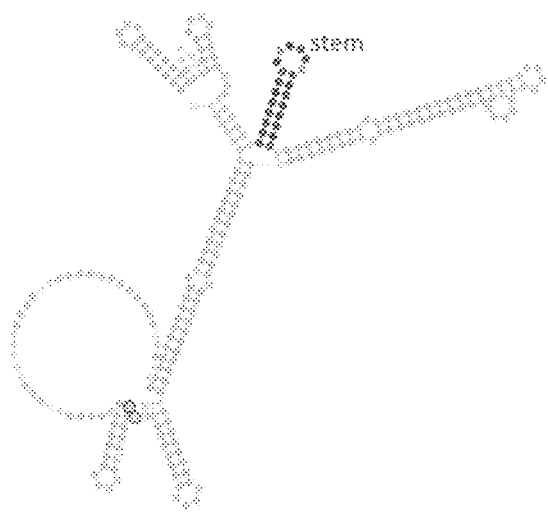
Figure 5F:
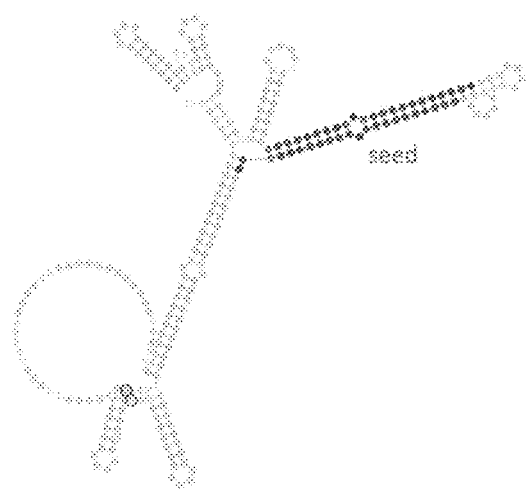
Figure 5G:
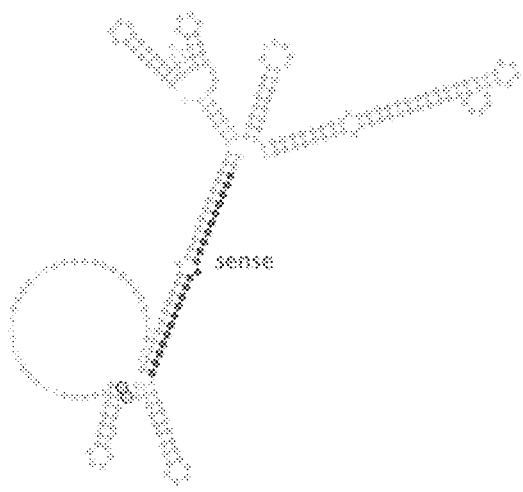
Figure 5H:
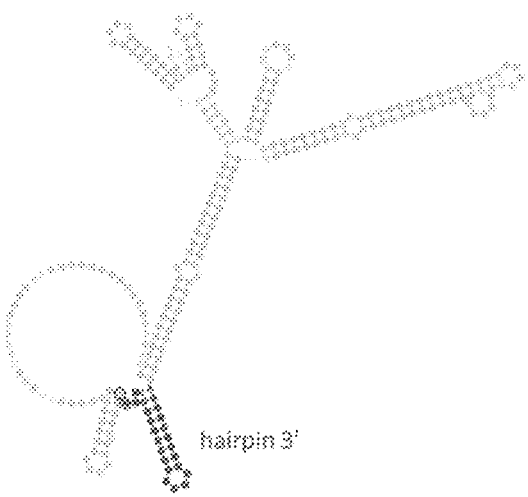

In other embodiments, the engineered RNA is an engineered sgRNA comprising, comprising: parts S-g-b-e-f-d-T-c-a-h (FIG. 4E, left panel). In other embodiments, herein the coding sequence for sgRNA comprises part S-g-b and a-h. In other embodiments, the responder sequence comprises parts e-f-d-T-c. In other embodiments, the actuator is a Cas protein. In other embodiments, in the absence of an input signal which comprises an input RNA that is completely or partially complementary to parts T-d-f, the engineered RNA forms a first secondary structure in which part d completely or partially hybridizes to part b, part e completely or partially hybridizes to part f, part a completely or partially hybridizes to part c, part g hybridizes to part h, and parts a and b are incapable of hybridizing with each other. In other embodiments, in the presence of the input RNA that is completely or partially complementary to parts T-d-f, the engineered RNA forms a second secondary structure in which parts T-d-f form a double strand with the input RNA, thereby releasing part e from part f and part b from part d, and in which part a partially hybridizes to part b to form a Cas protein binding site not at its lowest energy state.

It can be appreciated that any Cas protein or Cas protein variant can be employed herein. In some embodiments, the Cas protein is a Cas9 domain, for example a nuclease active Cas9, a Cas9 nickase (nCas9), or a nuclease inactive Cas9 (dCas9). Examples of Cas protein include, without limitation, Cas9 (e.g., dCas9 and nCas9), CasX, CasY, Cpf1, C2c1, C2c2, C2C3, saCas9, CjCas9, xCas9, Cas13a/C2c2, Cas13b, Cpf1 and variants thereof. Other Cas proteins are also within the scope of this disclosure, though they may not be specifically listed in this disclosure.

A Cas9 or Cas9 domain refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casnl nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gRNA") can be engineered so as to incorporate aspects of both the crRNA and tracrRNA into a single RNA species. See, e.g., Jinek M., Chylinski K., Fonfara I., Hauer M., Doudna J. A., Charpentier E. Science 337:816-821 (2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of Streptococcus pyogenes." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C.M., Gonzales K., Chao Y., Pirzada Z. A., Eckert M .R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but not limited to, S. pyogenes and S. thermophilus. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase. Additional suitable nuclease-inactive dCas9 domains will be apparent to those of skill in the art based on this disclosure and knowledge in the field, and are within the scope of this disclosure.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., Science. 337:816-821(2012); Qi et al., "Repurposing CRISPR as an RNA-Guided Platform for Sequence-Specific Control of Gene Expression" (2013) Cell. 28;152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of S. pyogenes Cas9 (Jinek et al., Science. 337:816-821(2012); Qi et al., Cell. 28;152(5):1173-83 (2013)). In some embodiments, proteins comprising Cas9 or fragments thereof are referred to as "Cas9 variants." A Cas9 variant shares homology to Cas9, or a fragment thereof.

In some embodiments, the Cas protein may be a fusion protein comprising a dCas9 domain and a functional protein. Non-limiting examples of Cas9 fusion proteins are dCas9-transcription factor, dCas9-VP64, dCas9-VPR, dCas9-Suntag, dCas9-P300, dCas9-VP160, dCas9VP192, dCas9-KRAB and its derivative, dCas9-MXI1, dCas9-SID4X, dCas9-LSD1, dCas9-CIB1, dCas9-GFP, and dCas9-RFP. Additional suitable Cas9 fusion proteins will be apparent to those of skill in the art based on this disclosure and knowledge in the field, and are within the scope of this disclosure.

Also within the scope of the present disclosure is an engineered nucleic acid that encodes the engineered RNA described herein. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, Molecular Cloning, A Laboratory Manual, 2012, Cold Spring Harbor Press).

In some embodiments, the engineered nucleic acids comprise a promoter operably linked to a nucleotide sequence encoding the engineered RNA described herein. A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is a constitutive promoter. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken (3-actin promoter. In some embodiments, a promoter is a U6 promoter.

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter. An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

Also within the scope of the present disclosure are cells comprising the engineered RNA described herein and the engineered nucleic acid encoding the same described herein. The cell can be any cell suitable for expressing the engineered RNA described herein. In some embodiments, the cells are prokaryotic cells. In some embodiments, the cells are bacteria cells. In other embodiments, the cells are eukaryotic cells. In some embodiments, the cells are mammalian cells. In other examples, the cells are human cells or non-human cells. Non-limiting example for non-human cells can be non-human mammalian cells, plant cells, insect cells, bacterial cells or fungal cells (including yeast cells). In some embodiments, the cell is a specific cell type in tissue. In some embodiments, the cell is a specific diseased cell. In some embodiments, the cell comprises the input signal necessary to trigger the conformational change of the engineered RNA. In some embodiments, the cell is a disease cell. In some embodiments, the cell is from a specific tissue. Non-limiting examples of the tissues are lung tissue, skin tissue, breast tissue, connective tissue, brain tissue, gastrointestinal tissue, heart tissue, kidney tissue, etc. Non-limiting examples for specific cell types are epithelial cells, endothelial cells, fibroblasts, immune cells, etc. Non-limiting examples of a diseased cells are neo-plastic cells, infected cells, cells harboring genetic mutations, fibro genetic cells, etc. The engineered RNA described herein, the engineered nucleic acid and/or the vectors can be delivered to the cells by methods known in the art. Non-limiting methods of delivery is transfection (e.g., electroporation, or liposome), viral particles (e.g., adeno-associated virus), nanoparticles (e.g., lipid nanoparticles), or genomic integration. In some embodiments, the engineered nucleic acid described herein is integrated into the genomic DNA of the cell. Genomic integration of the present engineered nucleic acid can be done by methods known in the art. In some embodiments, the genomic integration of the present engineered nucleic acid can be achieved by viral transduction (e.g., including but not limited to lentiviral vectors, retroviral vectors, PiggyBac transposon vector and SleepingBeauty transposon vector) and introduced into host immune cells using conventional recombinant technology. Sambrook et al., Molecular Cloning, A Laboratory Manual, 3rd Ed., Cold Spring Harbor Laboratory Press.

Also provided herein are organisms comprising the engineered RNA, the engineered nucleic acid encoding the same, the vector and/or cells described herein. Exemplary organisms can be prokaryotic organisms or eukaryotic organisms. In some embodiments, the prokaryotic organism is a bacteria. In some embodiments, the eukaryotic organism is an animal, a plant, or a fungus. In some embodiments, the eukaryotic organism is an animal. In some further examples, the animal is a non-human animal. Non-limiting examples of non-human animals are mice, chickens, goats, rabbits, pigs, donkeys, cows, or camels.

II. RECOMBINANT VIRUSES FOR DELIVERY OF THE ENGINEERED RNA

Also within the scope of the present disclosure are the delivery of the engineered nucleic acid encoding the engineered RNA described herein by recombinant viruses. Non-limiting examples of such recombinant viruses are adeno-associated viruses, lentivirus, alphavirus, adeno virus, or bacteriophage.

In some embodiments, the engineered nucleic acid encoding the engineered RNA described herein are delivered by adeno-associated viruses (AAV). The engineered nucleic acid encoding the engineered RNA described herein may be recombinant adeno-associated virus (AAV) vectors (rAAV vectors). In some embodiments, an engineered nucleic acid encoding the engineered RNA described herein as described by the disclosure comprises a first adeno-associated virus (AAV) inverted terminal repeat (ITR) and a second AAV ITR, or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The engineered RNA described herein coding sequence may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the engineered RNA described herein coding sequence, in which the selected the engineered RNA described herein coding sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; and when desired, sequences that enhance secretion of the encoded product. A number of expression control sequences, including promoters which are native, constitutive, inducible and/or tissue-specific, are known in the art and may be utilized. In some embodiments, the engineered RNA described herein coding sequence is operably linked to a suitable promoter described herein above.

In some aspects, the disclosure provides isolated AAVs (e.g., rAAVs encoding the engineered RNA described herein). As used herein with respect to AAVs, the term "isolated" refers to an AAV that has been artificially produced or obtained. Isolated AAVs may be produced using recombinant methods. Such AAVs are referred to herein as "recombinant AAVs." Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, an rAAV expressing the engineered RNA described herein is capable of increasing tissue or cell specificity such that the engineered RNA described herein can only function in the cells having the input signal that the rAAV can infect.

Methods for obtaining recombinant AAVs (e.g., encoding the engineered RNA described herein) having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, the rAAV (e.g., encoding the engineered RNA described herein) comprises an AAV capsid protein is of an AAV serotype selected from the group consisting of AAV2, AAV3, AAV4, AAV5, AAV6, AAV8, AAVrh8, AAV9, and AAV10.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

In some embodiments, an rAAV described herein (e.g., encoding the engineered RNA described herein) is a single stranded rAAV. An ssAAV, as used herein, refers to a rAAV with the coding sequence and complementary sequence of the transgene expression cassette on separate strands and are packaged in separate viral capsids. In some embodiments, the rAAV (e.g., encoding the engineered RNA described herein) is a self-complementary AAV (scAAV). A scAAV, as used herein, refers to an rAAV with both the coding and complementary sequence of the transgene expression cassette are present on each plus-and minus-strand genome. The coding region of a scAAV was designed to form an intramolecular double-stranded DNA template. Upon infection, rather than waiting for cell mediated synthesis of the second strand, the two complementary halves of scAAV will associate to form one double stranded DNA (dsDNA) unit that is ready for immediate replication and transcription.

In some embodiments, when the engineered RNA is an sgRNA, the Cas protein is also provided to the cell by an rAAV. In some embodiments, the Cas protein is saCas9. In some embodiments, the saCas9 is delivered to the cell by a single rAAV. In some embodiments, the Cas protein is not saCas9. In some embodiments, the Cas protein can be delivered to the cell by a dual AAV system. In some embodiments, a first rAAV delivers a portion of the Cas protein, and a second rAAV delivers a second portion of the Cas protein. A full length Cas protein coding sequence can be produced by trans-splicing or by homologous recombination of the two AAV genome.

III. PHARMACEUTICAL COMPOSITIONS

In some aspects, the present disclosure, at least in part, relates to a pharmaceutical composition, comprising engineered RNA described herein, the engineered nucleic acid, the recombinant virus, the cells, as described herein. The pharmaceutical composition described herein may further comprise a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used for in vivo administration must be sterile. This is readily accomplished by, for example, filtration through sterile filtration membranes. The pharmaceutical compositions described herein may be placed into a container having a sterile access port, for example, an intravenous solution bag or vial having a stopper pierceable by a hypodermic injection needle.

In other embodiments, the pharmaceutical compositions described herein can be formulated for intra-muscular injection, intravenous injection, intratumoral injection or subcutaneous injection.

The pharmaceutical compositions described herein to be used in the present methods can comprise pharmaceutically acceptable carriers, buffer agents, excipients, salts, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises lipid nanoparticles which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In other examples, the pharmaceutical composition described herein can be formulated in sustained-release format. Suitable examples of sustained-release preparations include semipermeable matrices of solid hydrophobic polymers containing the engineered RNA described herein, the nucleic acid encoding the same, the recombinant virus encoding the same or the cell comprising the same, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

IV. THERAPEUTIC APPLICATIONS

The engineered RNAs, the engineered nucleic acids, the recombinant viruses, the host cells and the pharmaceutical compositions described herein can be used to treat various diseases (e.g., disease cells having the input signal).

To practice the method disclosed herein, an effective amount of any of the engineered RNAs, the engineered nucleic acids, the recombinant viruses, the host cells, or the pharmaceutical compositions described herein can be administered to a subject (e.g., a human) in need of the treatment via a suitable route, such as intratumoral administration, by intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, pharmaceutical composition described herein can be aerosolized using a fluorocarbon formulation and a metered dose inhaler, or inhaled as a lyophilized and milled powder. In some examples, the pharmaceutical composition described herein is formulated for intratumoral injection. In particular examples, the pharmaceutical composition may be administered to a subject (e.g., a human patient) via a local route, for example, injected to a local site such as a tumor site or an infectious site.

As used herein, "an effective amount" refers to the amount of each active agent required to confer therapeutic effect on the subject, either alone or in combination with one or more other active agents. For example, the therapeutic effect can be reduced tumor burden, reduction of cancer cells, increased immune activity, reduction of a mutated protein, reduction of over-active immune response. Determination of whether an amount of engineered RNA described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of pharmaceutical composition described herein may be appropriate. Various formulations and devices for achieving sustained release are known in the art.

In some embodiments, the treatment is a single injection of the engineered RNAs, the engineered nucleic acids, the recombinant viruses, the host cells or the pharmaceutical compositions described herein. In some embodiments, the method described herein comprises administering to a subject in need of the treatment (e.g., a human patient) one or multiple doses of the engineered RNAs, the engineered nucleic acids, the recombinant viruses, the host cells or the pharmaceutical compositions described herein.

In some example, dosages for an engineered RNA, engineered nucleic acid, recombinant virus, host cell or pharmaceutical composition described herein (each a "therapeutic comprising the engineered RNA described herein") may be determined empirically in individuals who have been given one or more administration(s) of such a therapeutic. Individuals are given incremental dosages of the engineered RNA, engineered nucleic acid, recombinant virus, host cell or pharmaceutical composition described herein. To assess efficacy of a therapeutic comprising the engineered RNA described herein, an indicator of the disease/disorder can be followed. For repeated administrations over several days or longer, depending on the condition, the treatment is sustained until a desired suppression of symptoms occurs or until sufficient therapeutic levels are achieved to alleviate a target disease or disorder, or a symptom thereof.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen of the therapeutic comprising the engineered RNA described herein used can vary over time.

For the purpose of the present disclosure, the appropriate dosage of the therapeutic comprising the engineered RNA described herein will depend on the specific miRNA signature of the cell and the miRNA to be expressed, the type and severity of the disease/disorder, the pharmaceutical composition described herein is administered for preventive or therapeutic purposes, previous therapy, the patient's clinical history and response to the engineered RNA described herein, and the discretion of the attending physician. A clinician may administer a therapeutic comprising the engineered RNA described herein, until a dosage is reached that achieves the desired result. Methods of determining whether a dosage resulted in the desired result would be evident to one of skill in the art. Administration of one or more therapeutic comprising the engineered RNA described herein can be continuous or intermittent, depending, for example, upon the recipient's physiological condition, whether the purpose of the administration is therapeutic or prophylactic, and other factors known to skilled practitioners. The administration of a therapeutic comprising the engineered RNA described herein may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

The subject to be treated by the methods described herein can be a mammal, such as a human, farm animals, sport animals, pets, primates, horses, dogs, cats, mice and rats. In one embodiment, the subject is a human.

In some embodiments, the subject may be a human patient having, suspected of having, or at risk for a disease. Non-limiting examples of diseases that are suitable for treatment with the therapeutics comprising the engineered RNA described herein include: Alpha-1 antitrypsin deficiency, Hypercholesterolemia, Hepatitis B infection, Liver adenoma due to HIV infection, Hepatitis C virus infection, Ornithine transcarbamylase deficiency, Hepatocellular carcinoma, Amyotrophic lateral sclerosis, Spinocerebellar ataxia type 1, Huntington's disease, Parkinson disease, Spinal and Bulbar muscular atrophy, Pyruvate dehydrogenase deficiency, Hyperplasia, obesity, facioscapulohumeral muscular dystrophy (FSHD), Nerve Injury-induced Neuropathic Pain, Age-related macular degeneration, Retinitis pigmentosa, heart failure, cardiomyopathy, cold-induced cardiovascular dysfunction, Asthma, Duchenne muscular dystrophy, infectious diseases, or cancer.

Non limiting examples of cancers include melanoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, gastric cancer, and various types of head and neck cancer, including squamous cell head and neck cancer. In some embodiments, the cancer can be melanoma, lung cancer, colorectal cancer, renal-cell cancer, urothelial carcinoma, or Hodgkin's lymphoma.

A subject having a target disease or disorder (e.g., cancer or an infectious disease) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

In some embodiments, a therapeutic comprising the engineered RNA described herein may be co-used with another suitable therapeutic agent (e.g., an anti-cancer agent an anti-viral agent, or an anti-bacterial agent) and/or other agents that serve to enhance effect of an engineered RNA described herein. In such combined therapy, the therapeutic comprising the engineered RNA described herein, and the additional therapeutic agent (e.g., an anti-cancer therapeutic agent or others described herein) may be administered to a subject in need of the treatment in a sequential manner, i.e., each therapeutic agent is administered at a different time. Alternatively, these therapeutic agents, or at least two of the agents, are administered to the subject in a substantially simultaneous manner. Combination therapy can also embrace the administration of the therapeutic comprising the engineered RNA described herein in further combination with other biologically active ingredients (e.g., a different anti-cancer agent) and non-drug therapies (e.g., surgery).

V. GENERAL TECHNIQUES

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Gene Therapy in Mammalian Cells by the Use of the Strand Displacement Reaction In recent years, the use of RNA technologies has been steadily increasing. A general framework for some of these RNA-based technologies is the one where an RNA molecule interacts with an input, changes conformation/folding state due to this interaction and then, as consequence of that, it interacts with an actuator. According to the specific design, the input and actuator can be proteins, protein complexes, RNAs or also small molecules.

While this framework is robust for its use in cell free settings, in some cases, it has not been possible to use it in genetically encoded circuits in mammalian cells. Here, the folding of the RNA after the transcription from DNA can lead the RNA in a conformation state that allows the RNA to interact with the actuator even in case the input is absent. These unwanted side reactions must be avoided to use this framework in genetically encode circuits for gene therapy.

The technology disclosed herein provides clear design principles to avoid these side reactions. It is based on the general idea that an RNA strand can still interact with its related actuator when the conformation of the RNA needed for this interaction is at an energy state that is far from the lowest one.

As an application of this technology, the use of the strand displacement reaction in genetically encoded constructs in mammalian cells was reliably and robustly enabled. Indeed, a genetically encoded trans-activated gate-miRNA and a genetically encoded trans-activated gate-gRNA (for cas9) were engineered; importantly, the same design principles can be applied to other CRISPR-based technologies. In these applications the inputs are RNAs and the actuators are respectively the Drosha complex and Cas9. The inputs interact with the gates through the strand displacement reaction, but this is not limited to. Indeed, the technology disclosed herein can be used with any technology that uses the above-mentioned general framework.

The trans-activated gate-miRNA and the trans-activated gate-gRNA disclosed herein are currently the only genetically encoded constructs that allow respectively the down-regulation of an endogenous gene and DNA editing only in response to a specific RNAs biomarker signature. This will finally allow the conditional expression of therapeutic agents in cells that are characterized by RNAs biomarkers instead of miRNAs biomarkers. Additionally, both genetic constructs require a small DNA footprint and can be successfully delivered in vivo for gene therapy by the use of the AAV virus, which is considered among the safest viral vectors for the delivery of exogenous DNA in vivo. Finally, the trans-activated gate-miRNA does not use any exogenous protein and thus can be used in gene therapy drastically reducing the likelihood of unwanted and dangerous immune responses.

RNA is a versatile molecule that can be engineered in order to have RNA-RNA, Protein-RNA or small molecule-RNA interactions. A general framework for these interactions is shown in FIG. 1A. In this framework, an RNA strand can be seen as made by two parts, A and B. This RNA strand is usually designed such that, at its lowest energy level, part A can interact with an input, which according to the design can be another RNA, a protein or a protein complex, or a small molecule, while part B cannot interact with an actuator. This happens because B is designed to be in a conformation B1 that impedes the interaction to happen. After the interaction with the input, B changes folding state going from B1 to B2. After that, the actuator, which according to the design can be another RNA, a protein or a protein complex, can interact with B2. According to this general framework, the action of the actuator is triggered only in the presence of the input.

Figure 1B:
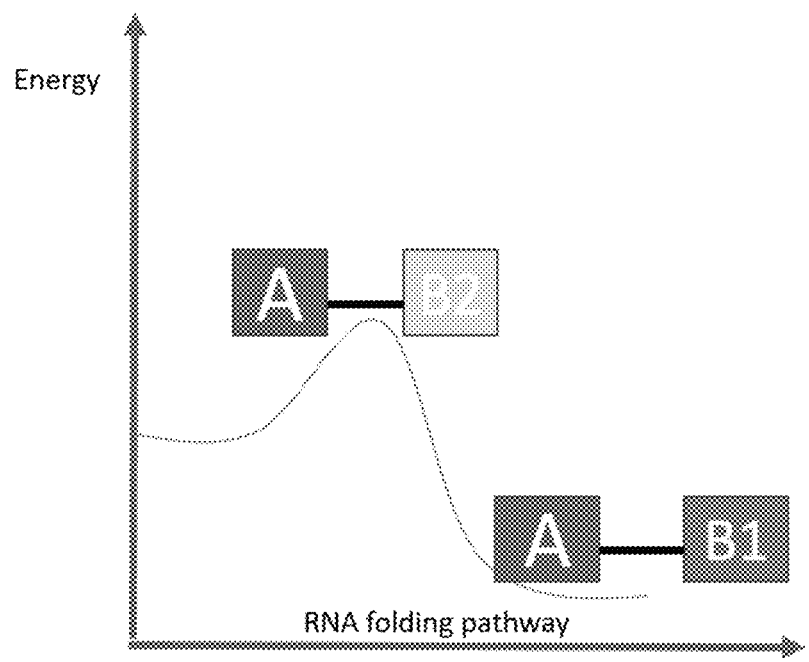

In cell free settings, technologies based on this framework have worked well. Usually, in these settings, first the RNA is let to fold at its lowest energy state and then is added to the samples containing the other components of the system like the input and actuator. Another way to use these technologies has been the delivery of an already folded RNA to living cells. Currently, the main obstacle to overcome for the use of some of these technologies in genetically encoded circuits is a drastic reduction of the side effects due to the folding of the RNA in living cells after its transcription from DNA. Indeed, when the RNA strand folds (FIG. 1B) the strand can fold in the A-B2 conformation, with can allow the actuator to interact with B2 even in the case the input is not present. In a scenario where the actuator should be triggered just when a specific biomarker signature is present, this is something that must be avoided.

Figure 1C:
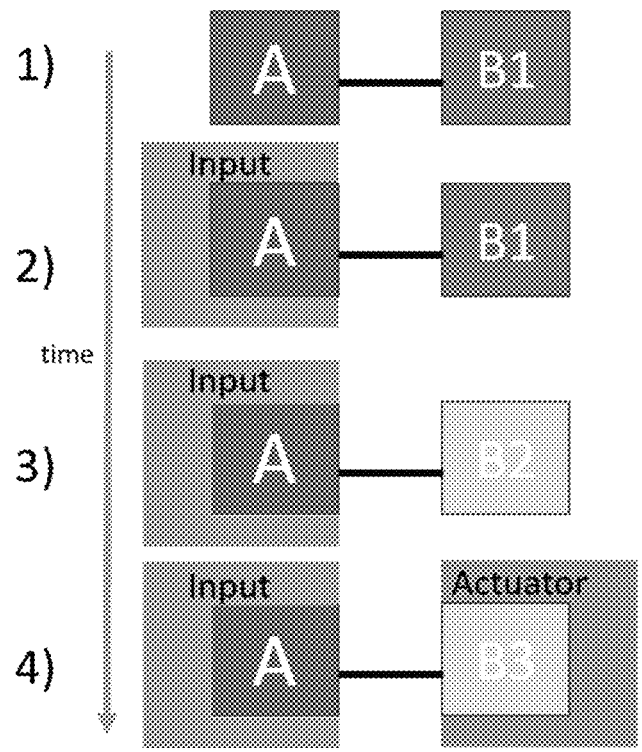
Figure 1D:
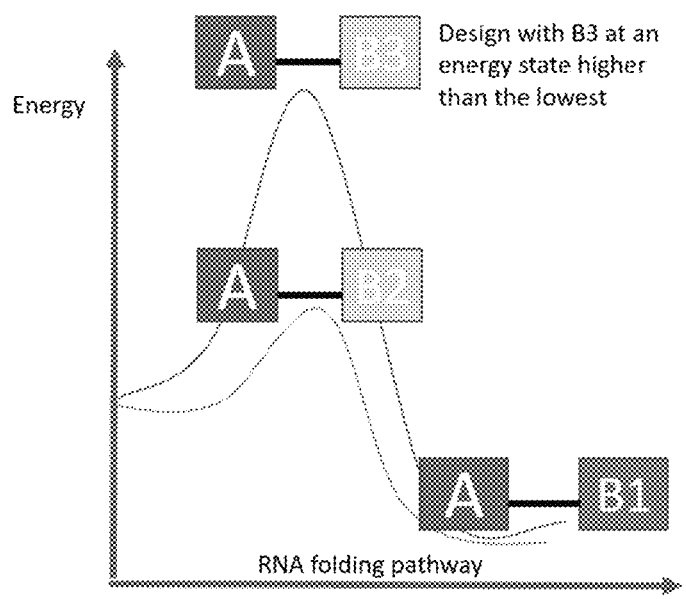
Figure 1E:
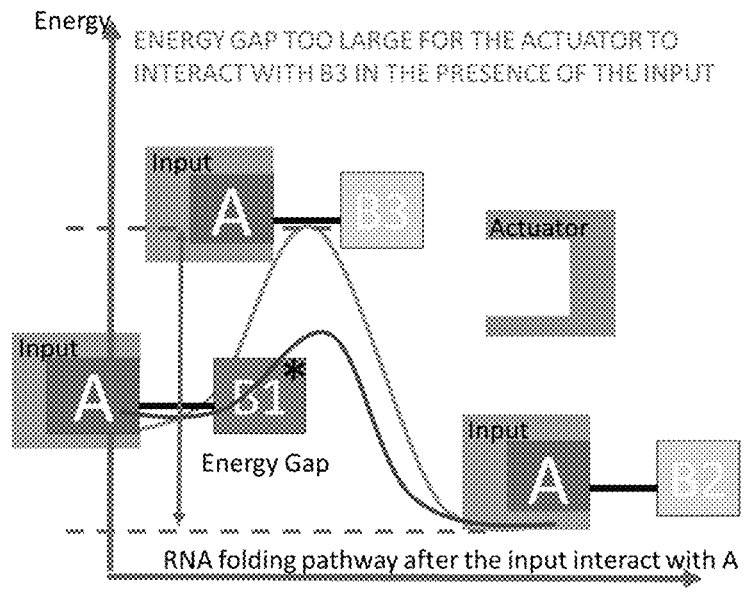
Figure 1F:
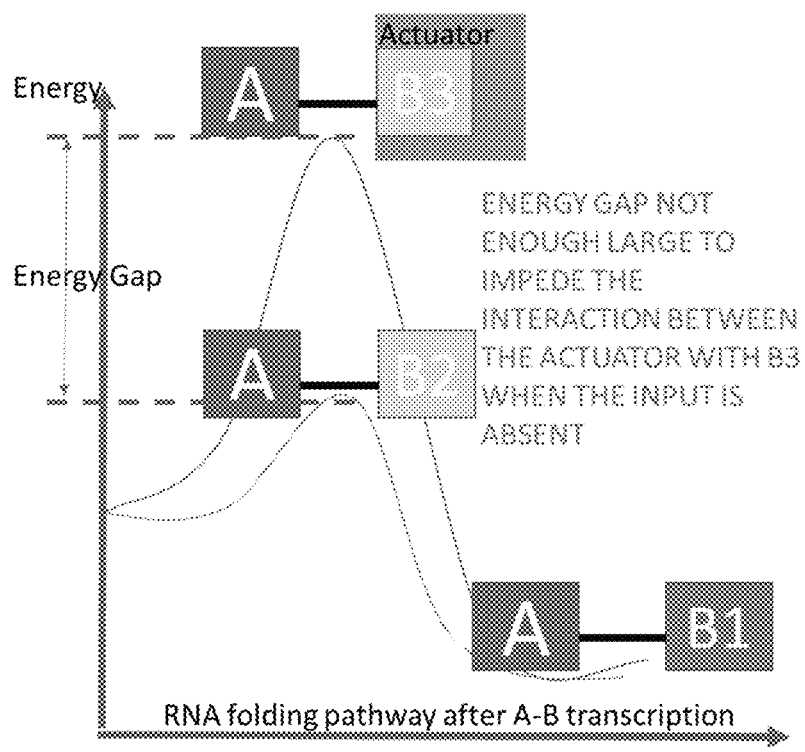

This technology drastically reduces these side reactions and it is based on the idea that B can still interact and trigger the activator in case it is designed to have this interaction at an energy state that is not its lowest (FIG. 1C); let's call B3 this conformation of B. As consequence of that, the energy barrier to overcome for the formation of B3 during the folding process will be higher (FIG. 1D) than the barrier in the case of B designed to interact with the actuator at its lowest energy state (FIG. 1D). A higher energy barrier makes it more unlikely for the RNA to form in the A-B3 conformation which in turn makes it more unlikely for the actuator to be triggered in the absence of the input (it is important to highlight that B at its lowest energy not necessarily is the same as B1, which is the conformation of the RNA strand B when A-B is at its lowest energy state before the interaction of the input with A).

Currently, modeling of the RNA folding dynamic is not sophisticated enough to predict whether an energy gap between B3 and B2 is too high to allow the interaction of B3 with the actuator after the input interacts with A. In the following, engineering design principles are disclosed that will allow the introduction of an energy gap between B2 and B3 and the experimental identification of the maximum of that gap. Those design principles are general and do not apply just to the strand displacement reaction.

In the strand displacement reaction, the input is another RNA strand while the actuator can be another RNA strand, a protein or a protein complex.

Using this technology in strand displacement reactions, genetically encoded trans-activated miRNA and trans-activated gRNA for cas9 have been engineered, where the activation is triggered by RNAs. This in turn will finally enable gene therapy for those diseases that are characterized by RNAs biomarkers signatures.

More in general, this technology can be used each time an endogenously transcribed RNA can interact with an actuator only in case an input triggers a change in conformation/folding of that RNA.

Example 2: Strand Displacement

Originally, the toehold-mediated strand displacement reaction has been used in cell free settings. There, a single strand DNA (or RNA) that will be called input (FIG. 2) interacts with a double stranded DNA (or RNA) that will be called gate. In this interaction, the input domain T*, that will be called toehold, anneal by Watson and Crick base pairing to the complementary T domain on the gate and then the domain Y2* displaces Y2. The input can itself be the output of an upstream system (FIG. 2), and the output of the strand displacement reaction can be the input of a system downstream. The gate is designed in its lowest energy state NOT to interact with the downstream system, whereas the output is usually designed to interact with the downstream system at the output's lowest energy state. According to the downstream system, the domain Y1 and X1 may or may not be present, can form secondary structures or have domains that bind to each other or change the way they interact with each other after the strand displacement happens. It is also common to have a gate where the X strand is 5' X2-X1 3' instead of 5' X1-X2 3' (still with X2 binding with Y2 by Watson and Crick base pairing). The output of the gate can be either the X1-X2 strand or the entire gate in its new conformation after the strand displacement reaction happens.

To avoid unwanted side reactions, in cell free settings, the gates are formed separately from each other, and then, all the parts of the system are put together. Each gate is usually formed by annealing two or more strands, but it can also be made by just one strand. For the same reason, for application in living mammalian cells, the gate are first formed separately in cell free settings and then transfected to cells.

The paper Sulc et al., "Modelling Toehold-Mediated RNA Strand Displacement. Biophys J. 2015 Mar. 10; 108(5): 1238-47." Present a mathematical model for kinetic and thermodynamic of the strand displacement reaction.

This technology provides a way to express endogenously transcribed engineered RNAs in mammalian cells, avoiding unwanted side reactions between the gate and the downstream system during the RNA folding process of the gate itself. This enables the use of the strand-displacement-based technology in genetically encoded logic circuits. Currently, in mammalian cells, the strand displacement reaction has been reliably used only in those cases where either the inputs or the gates were NOT endogenously transcribed. Indeed, when the gate is endogenously transcribed, because of the side reactions due to the RNA folding process, the background noise becomes too high. Endogenously transcribed inputs cannot reach a concentration high enough to trigger the gate beyond the noise level. So far, this has impeded the use of strand displacement in gene therapy. In order to use strand displacement as reliable tool in gene therapy, it is necessary to have endogenously transcribed gates that can interact with endogenously transcribed inputs. This would allow the possibility to sense basically any RNA biomarkers of choice. The technology disclosed herein allows the design of genetically encoded logic gates that respond to RNAs biomarkers that are signature of diseases in mammalian cells, but this is not limited to. Currently, without this technology, this would not be possible.

For instance, in the article Guo et al., "Recent advances in molecular machines based on toehold-mediated strand displacement reaction," the authors show systems where gates are endogenously transcribed in mammalian cells but not the inputs. The paper written by Wu et al., "A Survey of Advancements in Nucleic Acid-based Logic Gates and Computing for Applications in Biotechnology and biomedicine" show just a genetically encoded system that process miRNAs but not RNAs. Additionally, the gates of the system based on strand displacement are not endogenously transcribed. The paper written by Chen et al., "A DNA logic gate based on strand displacement reaction and rolling circle amplification, responding to multiple low-abundance DNA fragment input signals, and its application in detecting miRNAs" and the one written by Deng et al., "DNA Logic Gate Based on Metallo-Toehold Strand Displacement" show systems were the gates are not endogenously transcribed.

Example 3: Design of Trans-Activated Engineered RNA by Strand Displacement

Currently, this technology is the only one that can allow the use of the strand displacement reaction in mammalian cells in genetically encoded circuits. As consequence, this is the only technology that can allow to engineer these circuits for gene therapy in diseases that are characterized by RNAs biomarkers signature instead of miRNAs signatures.

This technology is based on the idea that the output of a strand displacement reaction can still interact with its downstream target when this interaction is designed to happen with the output strand not at its lowest energy state On the other hand, the gate is still designed such that, at its lowest energy state, it does not interact with the downstream system in the absence of the strand displacement reaction with the input. This design drastically reduces unwanted side reactions between the output strand and the downstream system during the folding of the RNA-transcript-gate in genetically encoded logic circuits. Indeed, the output signal now interacts with the downstream system far from its lowest energy state. Consequently, it will be more unlikely that, during the folding of the gate-RNA-transcript, the part of this transcript that correspond to the output will reach that energy state that is far from its lowest one.

In order to tune the energy states at which the output interacts with the downstream system, in the following design principles are provided and used to engineer a trans-activated sgRNA for Cas9 and a trans-activated miRNA.

One possible way to tune the energy state at which the output signal interacts with the downstream system is the following: First, a RNA strand domain is identified in the output, which will be called 'a' that has to bind to another RNA strand domain of the output, that will be called 'b', for the output of the strand displacement reaction to interact with the downstream system (the actuator). After that, it can be inserted in the output a new strand domain, that will be called 'c', which binds with 'a' more strongly than 'a' binding to 'b'. At the same time, the RNA structure formed by 'c' binding 'a' should not allow the output to interact with the downstream system. By tuning the binding energy between 'c' and 'a' it is possible to tune the energy gap between the lowest energy state of the output and the one that allows the output to interact with the downstream system.

Then, the maximum value of that energy gap that still allows B3 to interact with the actuator is experimentally determined. It is possible for instance to reduce the number of mismatches between 'c' and 'a' to increase the energy gap. The B3 conformation strand that will be no more able to interact with the actuator will set an upper limit for that energy gap. The chosen energy gap will be the one just below that limit. The same idea can be used in case the downstream system requires an RNA strand domain in the output to be single stranded (like when the downstream system is another gate to be strand displaced. Here, the single stranded RNA domain can be the toehold, but this is not limited to). Calling again 'a' this single stranded RNA domain, it is possible to insert in the output a new strand domain, that again will be called 'c', where 'a' and 'c' binds each other. Again in this case, by tuning the binding energy between 'a' and 'c', it is possible to tune the energy gap between the lowest energy of the output and the one at which the output can interact with the downstream system.

Trans-Activated miRNA miRNAs can downregulate coding genes. One way to genetically encode miRNAs, but this is not limited to, is to endogenously transcribe pre-miRNA that are later processed by Drosha, which in turn starts the miRNA biogenesis. In the left column of FIG. 3A, the substrate for Drosha processing is depicted. Drosha recognizes in the nucleus the RNA secondary structures depicted in orange. The Green part is later processed by the Dicer in the cytosol and, after that, one of the two red strands (usually their length is around 22nts) is loaded into the RISC complex that will then downregulate the expression of the target gene. The following is an excerpt from "The current state and future directions of RNAi-based therapeutics" Setten et al., Nature Reviews I Drug Discovery 2019: 'To date, there is not yet a published system that can reliably couple cellular RNA inputs to RNAi outputs in mammalian cells.'.

The technology disclosed herein enables exactly that. This is the only technology to allow to engineer a genetically encoded miRNA that is activated only when an endogenous RNA is transcribed. Importantly, the system does not use exogenous proteins and has a small DNA footprint, because of that it can be used with AAV to easily deliver it in vivo and to reduce unwanted immune reactions. Here, the design is provided for an endogenously transcribed trans-activated miRNA triggered by the toehold-mediated strand displacement reaction due to an endogenously transcribed RNA input strand. The input sequence is orthogonal to the sequence loaded in the RISC complex. Additionally, the RNAs secondary structures recognized by Drosha are loosely constrained by specific sequences and so they do not constraint the choice of the input sequence.

A similar design could be used to engineer a Dicer-trans-activated miRNA.

Figure 3A:
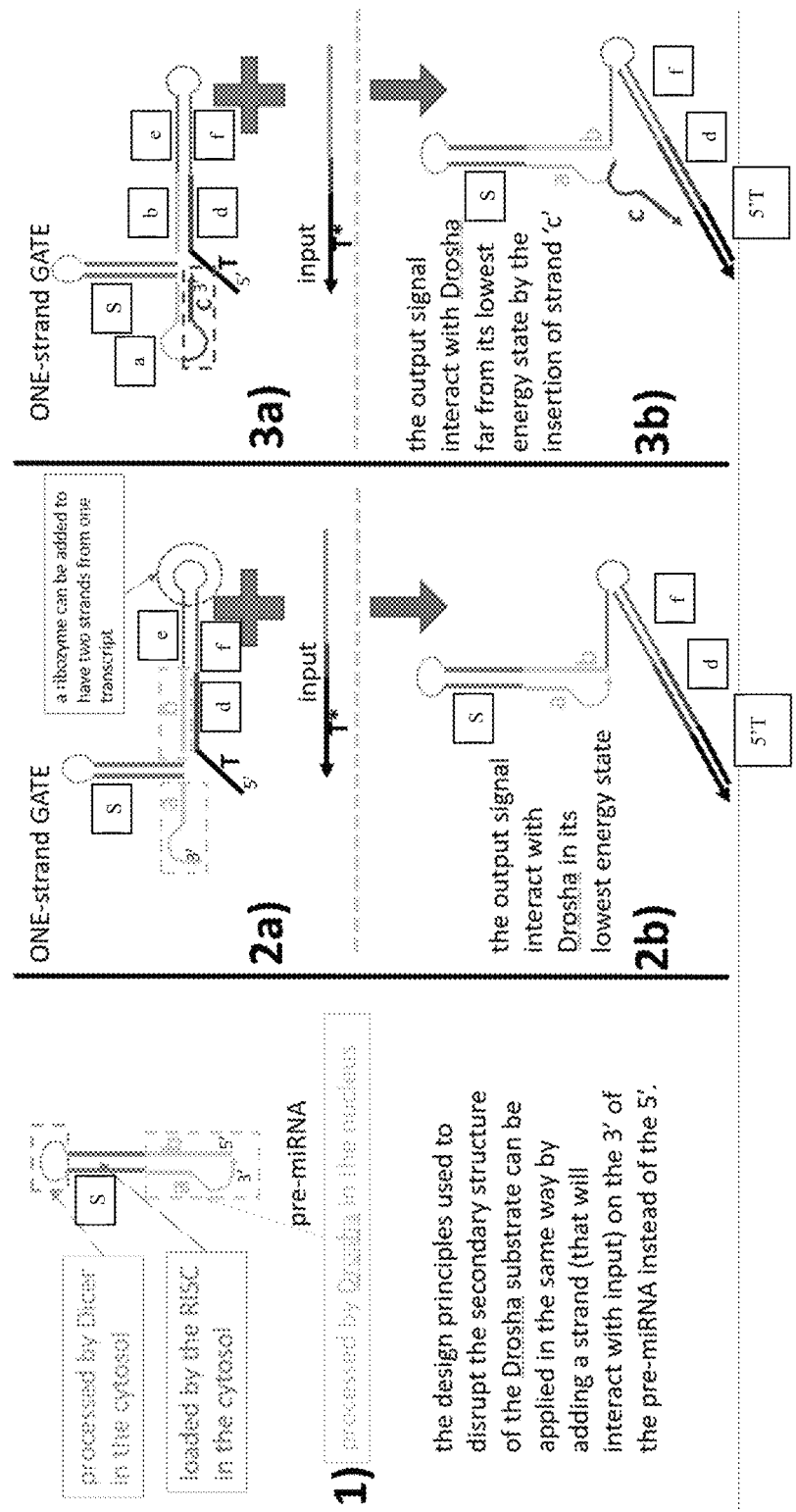
FIG. 3A-3G shows a design of engineering trans-activated miRNA by the use of the strand displacement reaction.

In left column of FIG. 3A, the design of the one-strand-gate with the output of the strand displacement reaction that interact with Drosha (which is the downstream system) at its lowest energy state (center column of FIG. 3A). This design requires that, after the strand displacement reaction, the strand 'a' binds to the strand 'b' in order for the processing by Drosha to take place. By expressing this gate in living cells, during the folding process of the gate-RNA-transcript, the Drosha-substrate can be processed by Drosha even in the absence of the input. This makes the detection of the input not possible. Because of that and according to the design principles mentioned before, a new strand 'c' was introduced that binds with 'a' more strongly than 'a' binding with 'b' (right column of FIG. 3A). This still allows the gate, in its lowest energy state, to avoid interaction with the downstream system (Drosha). However, this time, after the strand displacement reaction happens (right column of FIG. 3A), the output is processed by Drosha when the output is far from its lowest energy state.

Figure 3B:
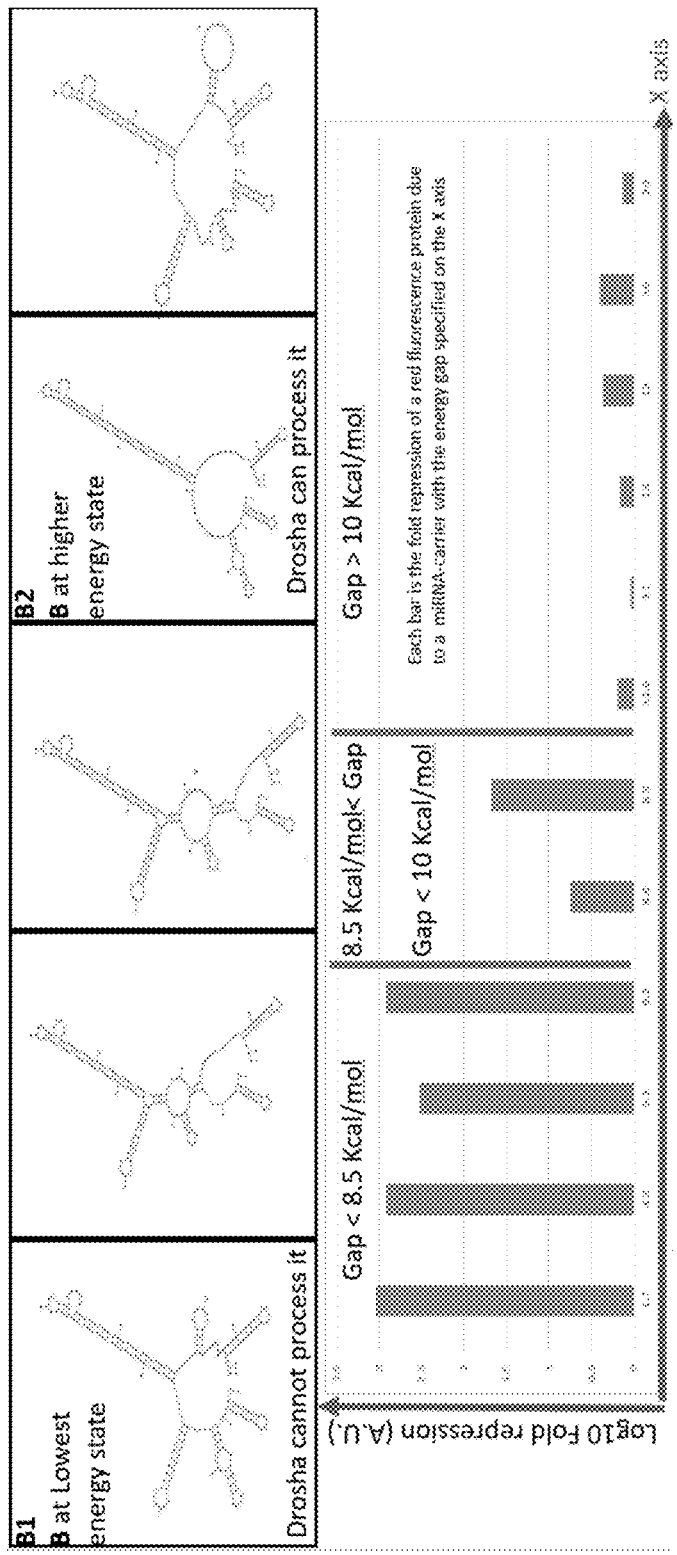
Figure 3C:
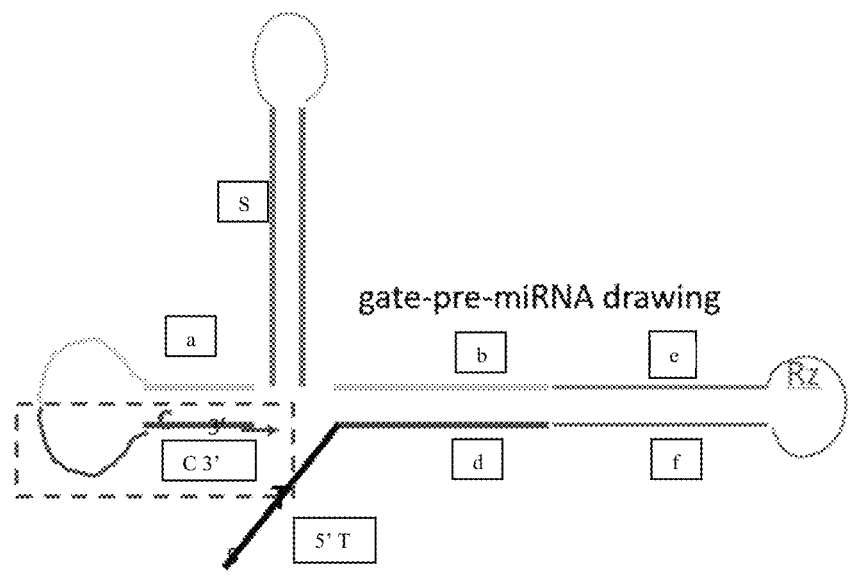
Figure 3D:
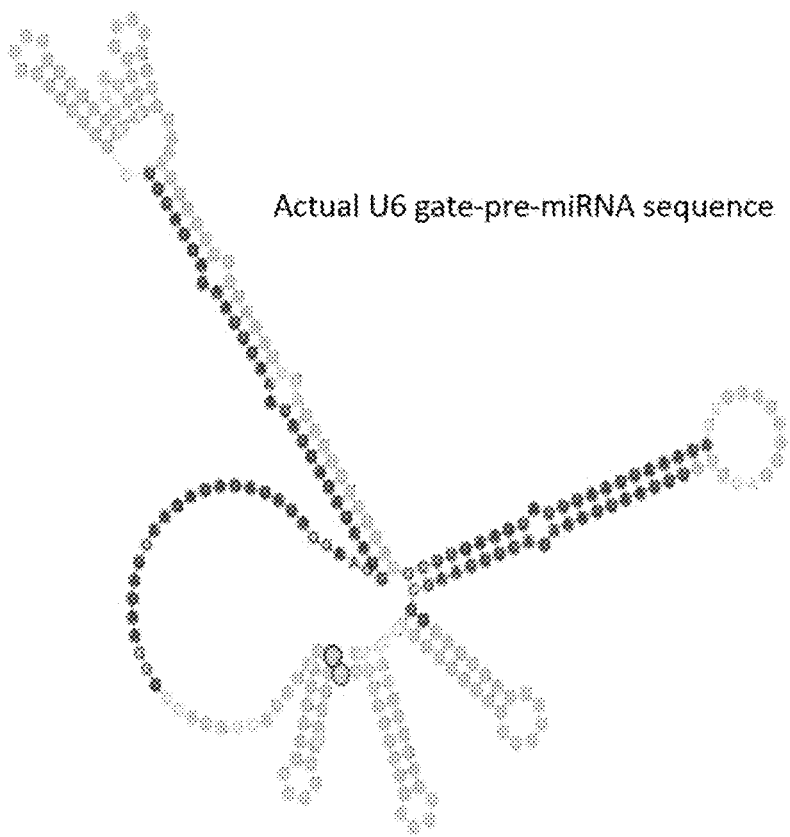
Figure 3E:
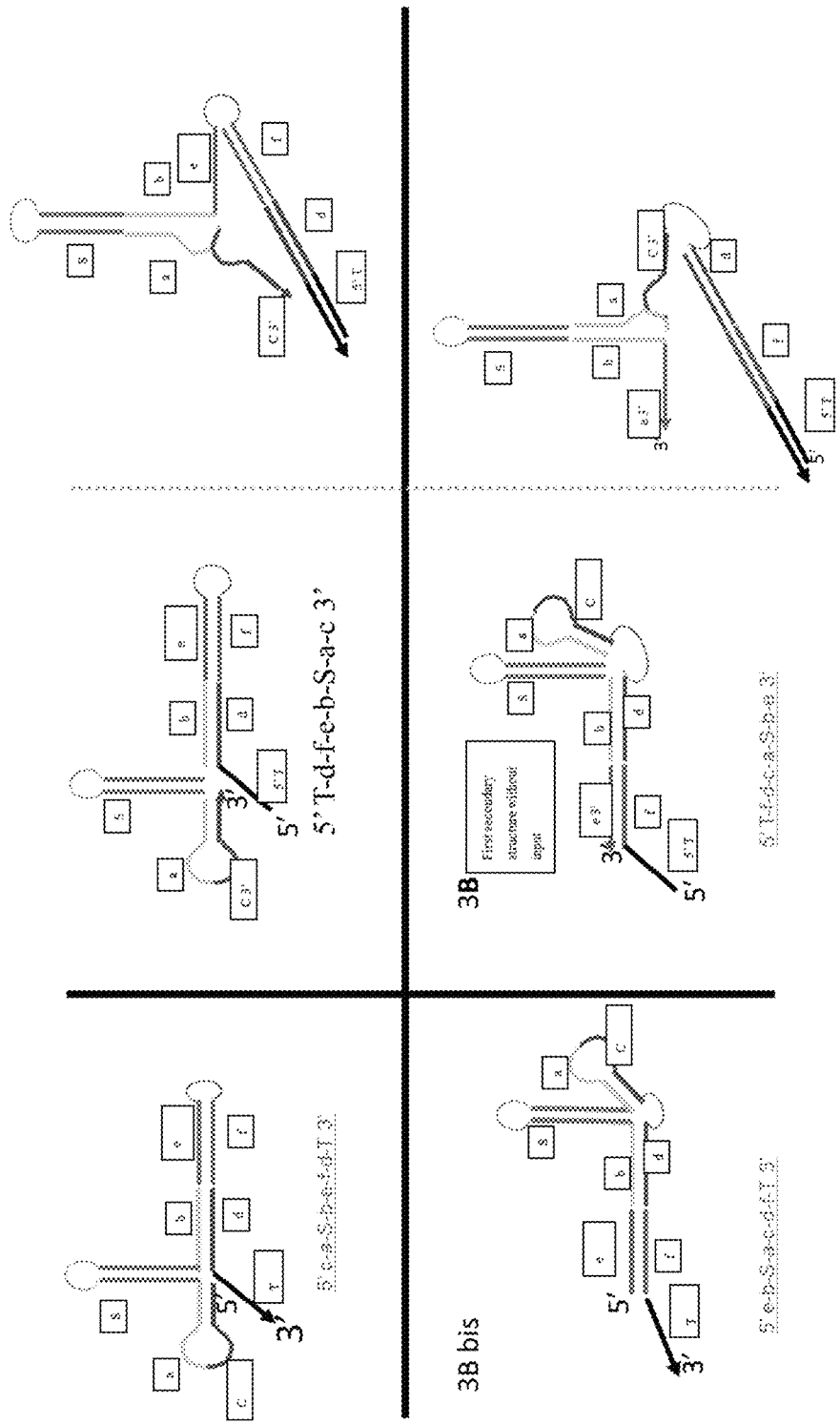
Figure 3F:
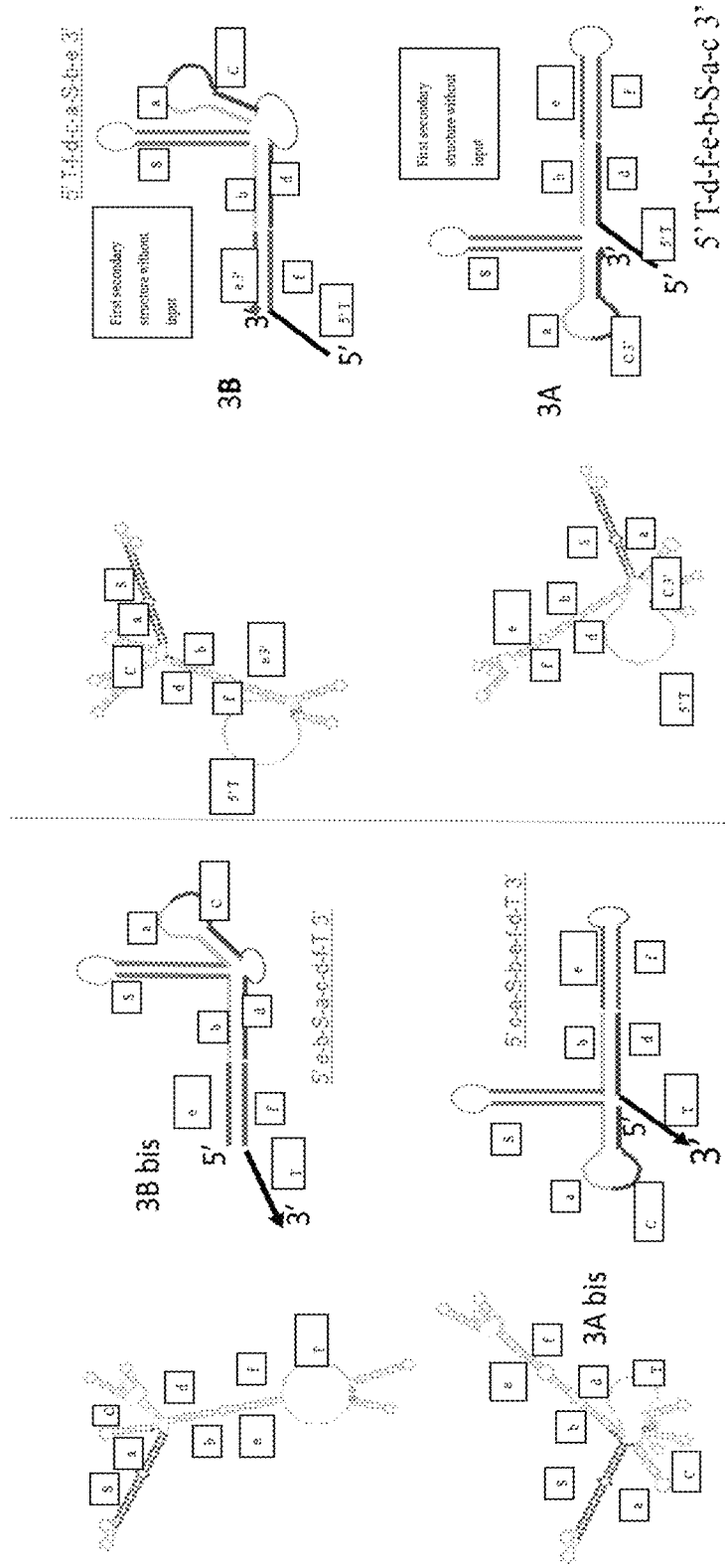

In FIG. 3B, the experimental results related to the investigation needed to find the upper limit of the energy gap. Thirteen different energy gaps were tested to identify what the limit was for Drosha to process the RNA. An energy gap between B2 and B3 less than 8.5 Kcal/mol allowed B3 to be still processed by Drosha. The energy gap was computed for each design using the software mFold (unafold.rna.albany.edu/?q=mfold). The introduction of this energy gap, drastically reduces the processing of the Drosha-substrate by Drosha during the folding of the gate-RNA-transcript, and so, it allows the detection of the input (it is more unlikely for A-B3 to form in the absence of the input). In FIGS. 3C-3D, the actual sequence of the trans-activated miRNA, while, in FIG. 3G, the experimental results in HEK293FT after transient transfection of the DNA encoding the different parts. FIGS. 3E-3F provides additional designs that adopts the same concept.

Figure 3G:
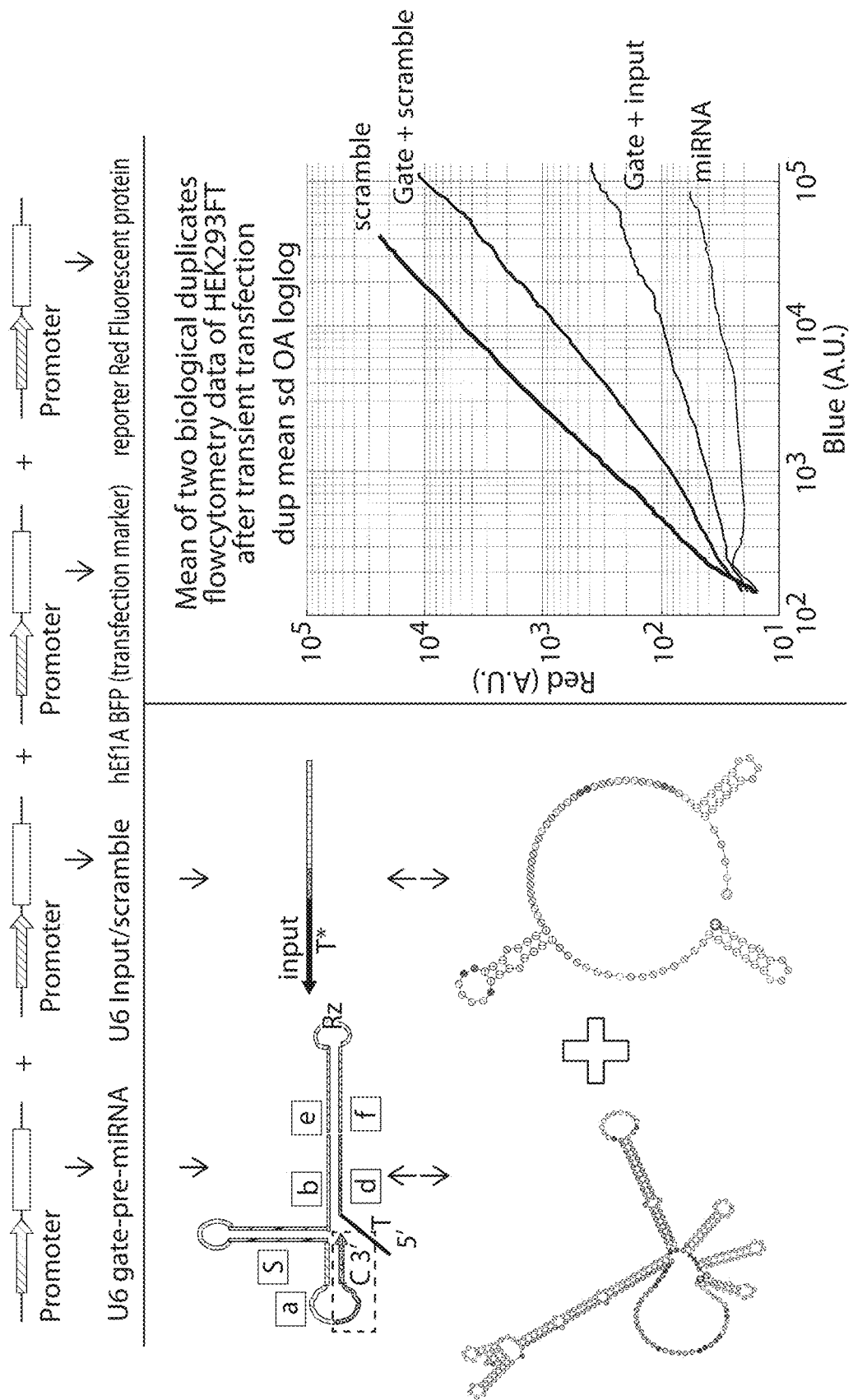

The difference in miRNA activation between the expression of an endogenously transcribed input and scramble is 30 folds, as shown in FIG. 3G.

Figure 6A:
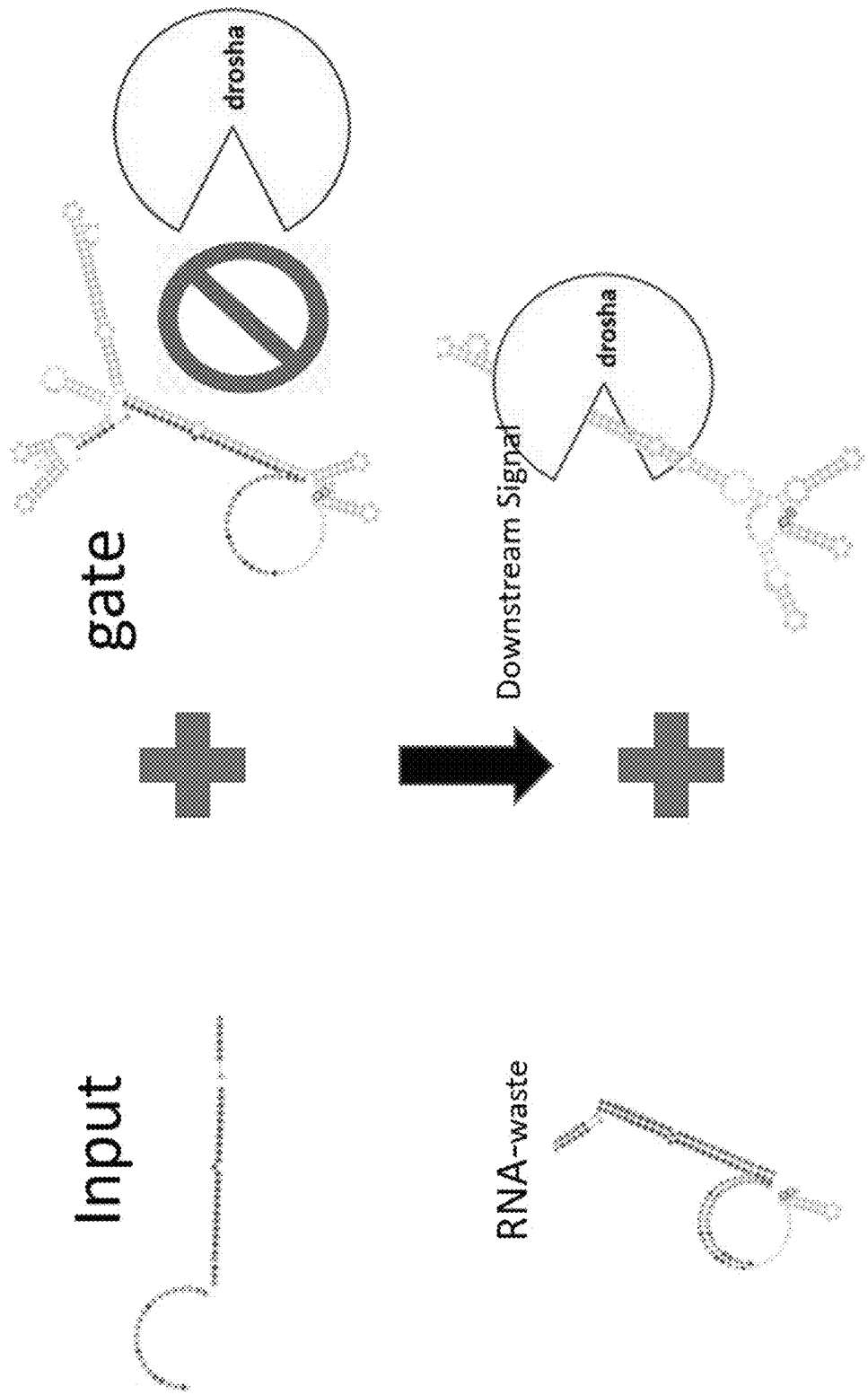
FIG. 6A-6D shows the possible secondary structures of an exemplary trans-activated miRNA.
Figure 6B:
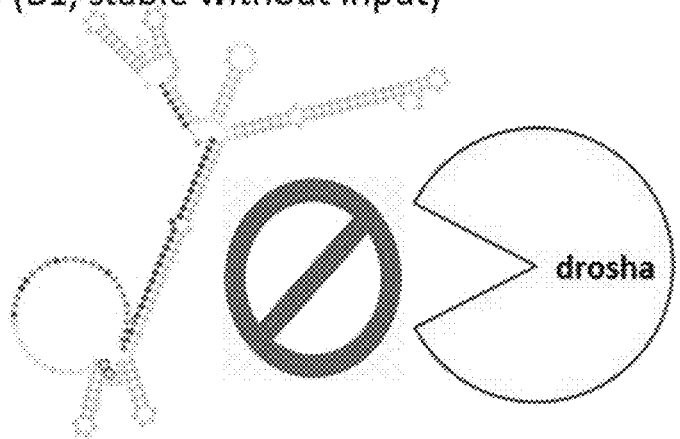
Figure 6C:
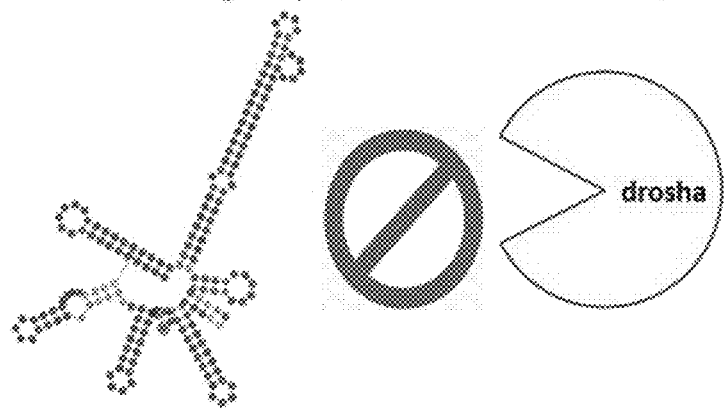
Figure 6D:
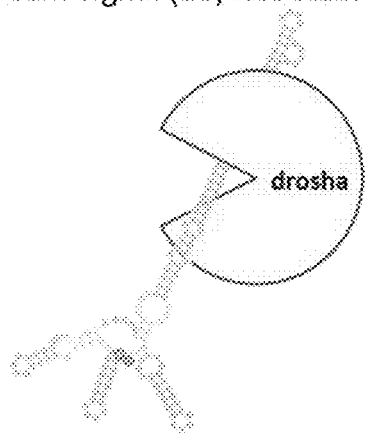
Figure 7:
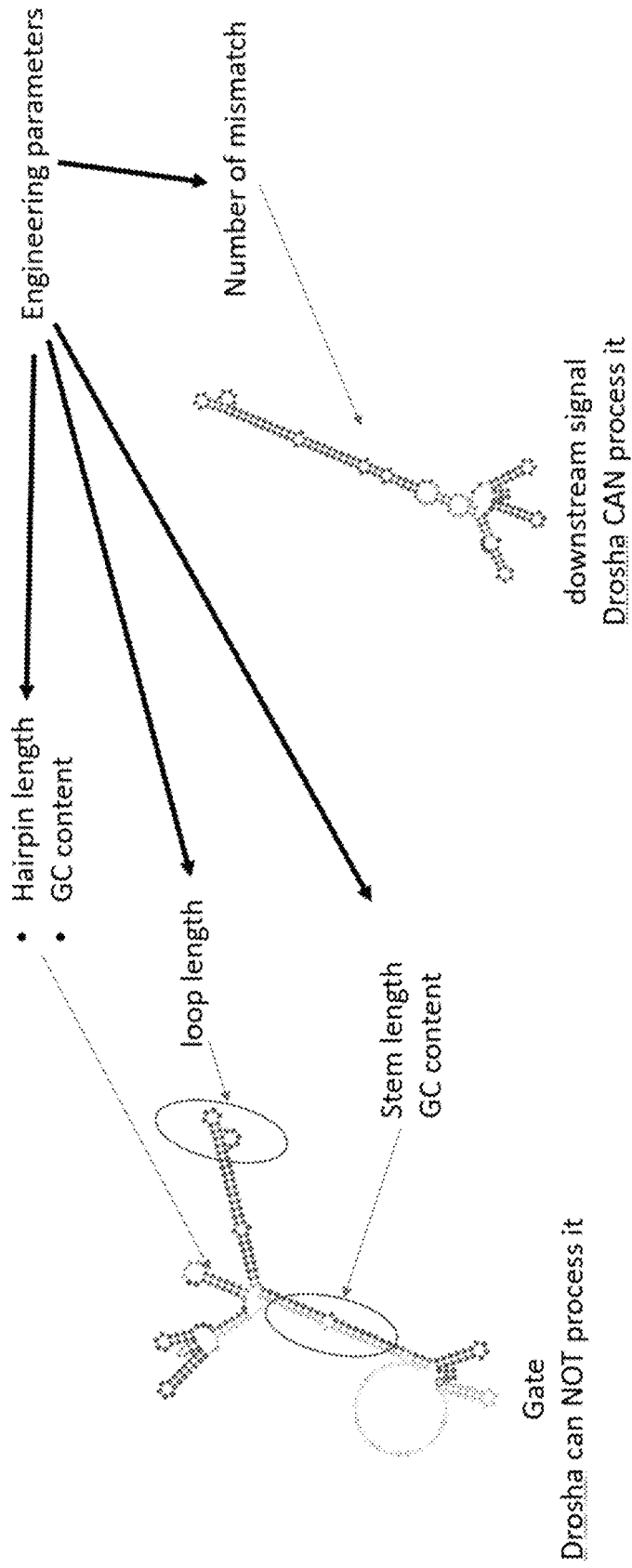
FIG. 7 shows the elements of a trans-activated miRNA that can be manipulated to change the dynamics of RNA folding and stability, which include hairpin length and GC content, loop length, stem length and GC content, and number of base mismatches.

The different domains of a trans-activated miRNA, including 5' hairpin, toehold, antisense, ribozyme, stem, seed, sense, and 3' hairpin, are shown in FIGS. 5A-5H. A schematic of this trans-activated miRNA interacting with input signal RNA is shown in FIG. 6A. In its native conformation, Drosha cannot interact with this RNA (FIG. 6B), but an input signal, such as an RNA associated with a disease state like viral infection, may hybridize to the trans-activated miRNA, resulting in the release of an RNA waste product by the ribozyme domain (FIG. 6A). Following this release, the trans-activated miRNA may undergo another conformational change, forming one of multiple possible structures, which may or may not be able to interact with Drosha and release pre-miRNA. The trans-activated miRNAs described herein are designed such that the more stable conformation cannot be processed by Drosha (FIG. 6C), but the less stable conformation can be processed by Drosha (FIG. 6D). These trans-activated miRNAs are thus less likely to interact with Drosha in the absence of input signal, which limits the release of pre-miRNA and biogenesis of miRNA against the therapeutic target to cells in which the input signal is present.

A major benefit of this increased specificity is that if they reliably exert activity only in cells containing the input signal, that activity can be directed towards the most effective target, even if that target is a gene that is essential for cellular replication. In the treatment of virally infected cells, for example, engineered RNAs such as the ones described in the present disclosure are not limited to targeting viral mRNAs, but may also target genes or mRNAs encoding host factors that are essential for viral replication. This increased specificity allows the engineered RNAs described in the present disclosure to target more genes or mRNAs, improving their therapeutic efficacy without compromising safety.

Trans-Activated sgRNA sgRNAs are small non-coding RNAs (FIG. 4) that can bind the protein cas9 for gene editing or other cas9-enabled applications. After the binding of cas9 to the sgRNA, cas9 is able to bind to a DNA sequence that is complementary to the spacer, which in turn triggers the cas9-enabled applications. Here, the design is provided of an endogenously transcribed trans-activated sgRNA by toehold mediated strand displacement due to an input that is endogenously transcribed as well.

Currently, this is the only technology to allow to engineer in mammalian cells a sgRNA that become active only when an RNA biomarker signature is detected. This in turn will enable DNA gene editing only in cells that express that RNA and thus will drastically reduce unwanted side reactions. Importantly, the system has a small DNA footprint, because of that, it can be used with AAV virus for easy delivery in vivo.

The input sequence is orthogonal with the spacer sequence. Additionally, the choice of the upper stem (FIG. 4A, left and center columns) for the engineering of the strand displacement reactions does not constraint the input sequence. This same idea can of course be applied to other stems of the sgRNA and to gRNA related to other-than-cas9 CRISPR proteins. In the center column of FIG. 4A, the design of a one-strand-gate with the output of the strand displacement reaction that interact with Cas9 (which is the downstream system) at its lowest energy state (center column of FIG. 4A). This design requires that, after the strand displacement reaction, the strand 'a' binds to the strand 'b' for the processing by Cas9 to take place. By endogenously transcribing this gate in living cells, during the folding process of the gate-RNA-transcript, unfortunately the sgRNA can be processed by Cas9 even in the absence of the input. This makes the detection of the input not possible. Because of that and according to the design principles mentioned before, new strand 'c' was introduced that binds with 'a' more strongly than 'a' binding with 'b' (right column of FIG. 4A). This still allows the gate to avoid interaction with the downstream system (Cas9) in its lowest energy state but this time, after the strand displacement reaction happens (right column of FIG. 4A) the output is processed by Cas9 when it is far from its lowest energy state.

FIGS. 4B-4C show the activated gRNA in the conformation B2 and B3. In this case as well, mFold was used to compute the energy state. The procedure is the same as for the pre-miRNA; by decreasing the number of mismatches between 'c' and 'a' the energy gap increases. This will lead to different designs to test experimentally. The upper limit for the energy gap will be the one where the gRNA in the B3 conformation will not be able anymore to be processed by cas9. The introduction of the energy gap drastically reduces the processing of the sgRNA by Cas9 during the folding of the gate-RNA-transcript and so it allows the detection of the input. FIGS. 4D and 4E provides additional designs of the trans-activated sgRNA based on the same concept In FIG. 4F, the experimental results in HEK293FT after transient transfection of the DNA encoding the different parts. The difference in Cas9 activation between the expression of an endogenously transcribed input and scramble is 8 folds.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An engineered RNA comprising,
  (i) an effector portion; and
  (ii) a responder sequence,
  wherein the effector portion comprises a coding sequence for a pre-microRNA (pre-miRNA),
  wherein, in the absence of an input signal, the engineered RNA forms a first secondary structure in which the engineered RNA is not capable of being recognized by an actuator;
  wherein, in the presence of the input signal, the responder sequence is capable of responding to the input signal such that the engineered RNA forms a second secondary structure, not at its lowest energy state, in which the engineered RNA is capable of being recognized by the actuator; and wherein the actuator is Drosha;
  (a) wherein the engineered RNA comprises parts T-d-f-e-b-S-a-c,
  wherein the coding sequence for a pre-miRNA comprises parts b-S-a,
  wherein the responder sequence comprises parts T-d-f-e,
  wherein, in the absence of an input signal which comprises an input RNA that is completely or partially complementary to parts T-d-f, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha, and
  wherein, in the presence of the input RNA that is completely or partially complementary to parts T-d-f, the engineered RNA forms a secondary structure in which parts T-d-f form a double strand with the input RNA, thereby releasing part e from part f and part b from part d, and in which part a partially hybridizes to part b to form a Drosha recognizable cleavage site not at its lowest energy state; or
  (b) wherein the engineered RNA comprises parts T-f-d-c-a-S-b-e,
  wherein the coding sequence for a pre-miRNA comprises parts b-S-a,
  wherein the responder sequence comprises parts T-f-d and e,
  wherein, in the absence of an input signal which comprises an input RNA that is completely or partially complementary to parts T-f-d, the engineered RNA forms a first secondary structure in which part d completely or partially hybridizes to part b, part e completely or partially hybridizes to part f, part a partially hybridizes to part c, and parts a and b are incapable of hybridizing with each other such that the engineered RNA is not capable of being recognized by Drosha, and
  wherein, in the presence of the input RNA that is completely or partially complementary to parts T-f-d, the engineered RNA forms a secondary structure in which parts T-f-d form a double strand with the input RNA, thereby releasing part e from part f and part b from part d, and in which part a partially hybridizes to part b to form a Drosha recognizable cleavage site not at its lowest energy state; or
  (c) wherein the engineered RNA comprises parts 5' hairpin-toehold-antisense-ribozyme-stem-seed-sense-3' hairpin,
  wherein the coding sequence for a pre-miRNA comprises parts stem-seed-sense,
  wherein the responder sequence comprises parts toehold-antisense-ribozyme,
  wherein, in the absence of an input signal which comprises an input RNA that is completely or partially complementary to parts toehold-antisense-ribozyme, the engineered RNA forms a first secondary structure in which part 5' hairpin completely or partially hybridizes to itself, part antisense completely or partially hybridizes to part sense, part ribozyme completely or partially hybridizes to itself, part stem completely or partially hybridizes to itself, part seed completely or partially hybridizes to itself, part 3' hairpin completely or partially hybridizes to itself, and part stem is incapable of hybridizing to part sense, such that the engineered RNA is not capable of being recognized by Drosha,
  wherein, in the presence of the input RNA that is completely or partially complementary to parts toehold-sense-ribozyme, the engineered RNA forms a secondary structure in which parts toehold-antisense-ribozyme hybridize with the input RNA, resulting in ribozyme-mediated cleavage that releases an RNA waste product comprising the input RNA hybridized to parts 5' hairpin-toehold-sense and a portion of part ribozyme of the engineered RNA, and wherein, following the release of the RNA waste product, the remaining portion of the engineered RNA forms a secondary structure in which part stem partially or completely hybridizes to part sense to form a Drosha recognizable cleavage site not at its lowest energy state.

2. The engineered RNA of claim 1, wherein miRNA is therapeutic miRNAs selected from the group consisting of miR-16, miR-29, miR-34, miR-143, miR-145, and miR-200 family.

3. An engineered nucleic acid, comprising a promoter operably linked to a nucleotide sequence encoding the engineered RNA of claim 1.

4. A recombinant virus, comprising: a viral capsid containing a promoter operably linked to a nucleotide sequence encoding the engineered RNA of claim 1.

5. An isolated cell, comprising the engineered RNA of claim 1.

6. The isolated cell of claim 5, wherein the isolated cell comprises the input signal.

7. A pharmaceutical composition, comprising the engineered RNA of claim 1.

8. The recombinant virus of claim 4, wherein the recombinant virus is a recombinant AAV (rAAV), lentivirus, adenovirus, or bacteriophage.

9. The isolated cell of claim 5, wherein the isolated cell is:
a) a eukaryotic cell;
b) a diseased cell; and/or
c) from a specific tissue.

10. The isolated cell of claim 5, wherein the isolated cell is a prokaryotic cell.

11. The isolated cell of claim 9, wherein the eukaryotic cell is a fungal cell, plant cell, insect cell, mammalian cell, or a human cell.

12. The isolated cell of claim 10, wherein the prokaryotic cell is a bacterial cell capable of processing the engineered RNA to produce the functional RNA.

* * * * *